(12) United States Patent
Estes

(10) Patent No.: US 7,249,117 B2
(45) Date of Patent: Jul. 24, 2007

(54) KNOWLEDGE DISCOVERY AGENT SYSTEM AND METHOD

(76) Inventor: Timothy W. Estes, 3028 Summit Pl., Birmingham, AL (US) 35243

( * ) Notice: Subject to any disclaimer, the term of this patent is extended or adjusted under 35 U.S.C. 154(b) by 410 days.

(21) Appl. No.: 10/443,653

(22) Filed: May 21, 2003

(65) Prior Publication Data

US 2006/0112029 A1 May 25, 2006

Related U.S. Application Data

(60) Provisional application No. 60/382,503, filed on May 22, 2002.

(51) Int. Cl.
*G06N 5/00* (2006.01)
*G06N 5/02* (2006.01)
*G06N 7/02* (2006.01)

(52) U.S. Cl. .............................. 706/52; 706/18; 706/55; 706/58

(58) Field of Classification Search ................... 706/52; 715/757
See application file for complete search history.

(56) References Cited

U.S. PATENT DOCUMENTS 6,247,002 B1 * 6/2001 Steels ......................... 706/20
6,283,761 B1 * 9/2001 Joao ............................ 434/236

OTHER PUBLICATIONS

James Henderson, A Connectionist Architecture with Inherent Systematicity, 1996, Department of Computer Science □□University of Exeter.*

Antony Browne et al., "Preprint of Paper 'Connectionist Inference Models' to appear in Neural Networks", 2001, p. 10.*

Numerical Recipes in C: The Art of Scientific Computing (ISBN 0-521-43108-5) Copyright (C) 1988-1992 by Cambridge University Press. Programs Copyright (C) 1988-1992 by Numerical Recipes Software.), Section 3.1 □□□□□.*

Shang et al., An Intelligent Distributed Environment for Active Learning, 2001, ACM 1-58113-348-0/01/0005.*

Boguraev et al., Applications of Term Identification Technology: Domain Description and Content Characterisation, 1999, Natural Language Engineering 5 (1): 17-44. □□.*

Rieger, Fuzzy Word Meaning Analysis and Representation in Linguistic Semantics. An Empirical Approach to the Reconstruction of Lexical Meanings in East- and West-German Newspaper Texts., 1980, German Department, Technical University of Aachen, Germany.*

Edward L. Waltz, Information Understanding: Integrating Data Fusion and Data Mining Processes, 0-7803-4455-3/98/ 1998 IEEE.*

* cited by examiner

*Primary Examiner*—Anthony Knight
*Assistant Examiner*—Nathan H. Brown, Jr.
(74) *Attorney, Agent, or Firm*—W. Edward Ramage; Baker Donelson

(57) ABSTRACT

A system and method for processing information in unstructured or structured form, comprising a computer running in a distributed network with one or more data agents. Associations of natural language artifacts may be learned from natural language artifacts in unstructured data sources, and semantic and syntactic relationships may be learned in structured data sources, using grouping based on a criteria of shared features that are dynamically determined without the use of a priori classifications, by employing conditional probability constraints.

38 Claims, 10 Drawing Sheets

58

| Element | ConceptID | Concept (C) | PredicateID | Predicate (P) | Object (CL) | Weight | URL | Position |
|---|---|---|---|---|---|---|---|---|
| Value | Int | String, MID | Int | String, MID | String, MID | Int | String | Int |

| Element | ModifierID (MID) | Modifier | Time (T) |
|---|---|---|---|
| Value | Int | String | String |

84

| Field | Semantic Unit (SM) | Count (C) | SMLink (SML) | Time (T) |
|---|---|---|---|---|
| *Value* | *array* | *int* | *array* | *string* |

KNOWLEDGE DISCOVERY AGENT SYSTEM AND METHOD

CROSS-REFERENCES TO RELATED APPLICATIONS

This application claims the benefit of U.S. Provisional Application No. 60/382,503, entitled "Knowledge Discovery Agent System and Method," filed May 22, 2002 by Timothy W. Estes, the specification, drawings, appendices and attachments of which are incorporated herein by reference.

TECHNICAL FIELD

The present invention relates to an artificial intelligence system and method. More particularly, the invention provides a system and method for producing intelligent software agents for interconnecting software and hardware platforms.

BACKGROUND OF THE INVENTION

The proliferation of specialized technology across multiple industries has led to an expanding problem of connecting together disparate information systems in a way that provides value that justifies the cost of creating interoperability. It is desirable to harness the collective knowledge of different systems for better management of intellectual assets, improved oversight of business or organization operations, and optimizing business or organization procedures. As the complexity of business or organization systems has grown and the IT components of business or organization processes have become more spread out, integration software has become more layered and segmented. Often, however, many current tools aimed at aggregating this information use poor methods for converting it into useable knowledge. These tools, often termed "middleware," are designed to connect systems, not enhance them or learn from them. Middleware which synthesizes integration, analytics, and process awareness into a package can create new functionality and efficiency while preserving past investments in software and hardware.

Other tools, such as knowledge management software, are able to make limited strides towards refining this collected information into useable knowledge. However, there exist few solutions that are able to take information from multiple sources and provide effective wrapping of services and knowledge management. Knowledge management software and its sister field, Business or Organization Intelligence (BI), are becoming critical to creating and maintaining competitive business or organization advantages within multiple industries. Tools that attempt to fulfill these needs run the gamut from simple document management and organization software to enhanced heuristic or case-based categorization systems to the most advanced systems utilizing natural language processors for tackling limited semantic awareness.

Software Agents have become more and more ubiquitous in software development in a variety of fields. These autonomous programs lend themselves to popular and diverse applications in such fields as web services (called "bots"), customer relationship management (CRM) enhancement, "software wrapping" industrial equipment, and wireless intelligent networking software. In particular, the idea of using intelligent agents as wrappers on legacy systems to make these systems and their software operational with new applications and platforms is very appealing and could provide an advantageous approach for industries having the most acute need for intelligent middleware.

Therefore, what is needed is needed is more intelligent middleware to meet these objectives.

SUMMARY OF THE INVENTION

In one exemplary embodiment, the present invention provides software that learns as it runs, in order to generate more valuable knowledge. Natural language analysis is used to tackle limited semantic awareness, thereby producing software that not only is semantically aware but actually achieves real semantic understanding through its proprietary knowledge creation and representation system.

In another exemplary embodiment, the invention creates superior communication between disparate computer systems. By thinly wrapping applications and data stores with intelligent agents, the present invention minimizes the overhead involved in connecting these systems while maximizing the range of services offered.

In yet another embodiment, the present invention provides intelligent middleware that enables businesses or organizations to access and share the accumulated wisdom of the members of its organization, which is normally fused into the processes and knowledge of an organization or business and diffused throughout its many systems and locations.

In a further embodiment, the invention provides advanced learning agents which extend the parameters for machine agent capabilities beyond simple, fixed tasks by learning on a continuous basis as they are used, thereby becoming smarter and able to do more complex tasks as well as enabling them to optimize their performance as they are run. Such agent capabilities lead to ever-expanding and increasingly-efficient delegation abilities in the agents. The invention thus may generate an improved return on the investment cost of software systems without requiring a particular business or organization to upgrade any of its software platforms, thereby producing great costs saving in future information technology expenses.

In another embodiment, the invention comprises a system for processing information, which may be termed a dynamic conceptual network system or knowledge discovery agent system. The system comprises: a computer for running software programs in a distributed network, the computer including a processing means in communication with the distributed network; at least one storage means in communication with the processing means for storing programs and information; and at least one data agent in the distributed network for conducting a specific response to commands generated by the processing means. The computer, the at least one storage means, and the at least one data agent are configured to be operable for learning associations of natural language artifacts. Natural language artifacts include, but are not limited to, phrases, predicates, modifiers, and other syntactic forms, in unstructured data sources. The computer, storage means, and data agent are further operable for learning semantic and syntactic relationships in structured data sources, wherein the structured data sources comprise entities in conventional formats used by relational database systems. The learned associations are formed using grouping of one natural language artifact in a interaction window, which can be of a fixed or relative size, with another at least one natural language artifact, based on a criteria of shared features of one or more sets from the grouping. This interaction window, which is also referred to in this disclosure as a "semantic unit," constitutes a range of measurement that approximates limited attentional perception by the processing agent or program and is the building block for measurements of conditional probability between one natural language artifact and another natural language artifact. The criteria for grouping are dynamically determined without the use of a priori classifications such as categories, topics, or classes, through satisfying conditional probability constraints between sets of learned associations.

The system may further comprise a means for representing learned associations in a specific format, wherein the specific format is compatible for operations for mapping between a plurality of data structures and languages comprising one or more of arrays, vector spaces, first order predicate logic, Conceptual Graphs, SQL, and typed programming languages. The typed program languages may include one or more of Java, C++, and other conventional programming languages.

The system may also comprise a means for constructing hierarchies of association across a state space of term usage compatible for interpolation of mapping functions between sets of terms, with the terms having particular syntactic positions. The mapping functions may include one or more of fuzzy-type, weighted-type, or other types of mapping functions. This system can further comprise means for generating a structure of mapping functions composed of sets of terms in particular syntactic positions, and wherein said structure is a formal semantic structure of one or more of programming languages, modal logics, frame systems, and ontologies of objects and relationships.

The system may further comprise means for collecting data input generated by interaction between the system and a human user, and means for learning from the input. Means for utilizing results of this learning by the sensors may also be provided, to reorganize and alter mapping functions induced from analyzed input. Also, means may be provided for aligning the mapping functions according to human natural usage information in the results. The input may be in the form of either structured data or unstructured data.

In yet another embodiment, the system may further comprise the following: a chatbot (also known as a "chatterbot" or "chat bot") comprising a chatbot engine for engaging in dialogue with a user through natural language; a conversational inference module for translating requests from the chatbot to the computer, the storage means, and the data agent or agents; and, one or more data extractors, connected to an existing third-party information system and operable for interfacing with this system in response to requests processed by the chatbot and the conversational inference module. The third-party information system may be a medical information system selected from the group comprising physician offices systems, hospital systems, corporate systems, and health care providers network systems.

One or more network data agents may also be provided in the system, for connecting at least one preselected physician information system to at least one health care provider network, and for extracting data from the preselected physician information system and providing the data to the health care provider network.

The system also may be utilized in government and security applications such as processing defense intelligence information, as by clustering and visualizing data which can be provided to a human analyst of defense intelligence as a supplemental tool.

In another embodiment of the present invention, a method for processing information is disclosed, which may be termed a dynamic conceptual network method or knowledge discovery agent method, comprising the following steps: providing a computer for running software programs in a distributed network, with the computer including a processing means in communication with the distributed network; providing at least one storage means in communication with the processing means, for storing programs and information; providing at least one data agent in the distributed network, for conducting a specific response to commands generated by the processing means; and, configuring the computer, at least one storage means, and at least one data agent to be operable for: learning associations of natural language artifacts in unstructured data sources, wherein the artifacts include at least one of phrases, predicates, modifiers, and other syntactic forms; and, learning semantic and syntactic relationships in structured data sources, wherein the structured data sources comprise entities in conventional formats used by relational database systems.

The learned associations resulting from the learning associations of natural language artifacts are formed using grouping of one natural language artifact in a interaction window, which can be of either a fixed or relative size, with another at least one natural language artifact in the interaction window, based on a criteria of shared features of one or more sets from the grouping. The criteria are dynamically determined without the use of a priori classifications such as categories, topics, or classes, through satisfying conditional probability constraints between sets of learned associations.

The method may further comprise the steps of: representing learned associations in a specific format, wherein the specific format is compatible for operations for mapping between a plurality of data structures and languages comprising one or more of arrays, vector spaces, first order predicate logic, Conceptual Graphs, SQL, and typed programming languages; and wherein the typed program languages comprise one or more of Java, C++, and other conventional programming languages. The method may further comprise the steps of constructing hierarchies of association across a state space of term usage compatible for interpolation of mapping functions between sets of terms, wherein the mapping functions include one or more of fuzzy-type, weighted-type, or other types of mapping functions, and wherein the sets of terms have corresponding particular syntactic positions.

In yet another embodiment, the method may comprise the steps of: generating a structure of mapping functions composed of sets of terms in particular syntactic positions, wherein the structure is a formal semantic structure of one or more of programming languages, modal logics, frame systems, and ontologies of objects and relationships; collecting data input generated by interaction with a human user; and, learning from said input. It may also comprise: utilizing results of the learning to reorganize and alter mapping functions induced from analyzed input; and, aligning the mapping functions according to human natural usage information in the results of the learning, wherein the input data is in the form of structured information or unstructured information.

The method may also comprise the following steps: providing a chatbot comprising a chatbot engine for engaging in dialogue with a user through natural language; providing a conversational inference module for translating requests from the chatbot to the computer, the at least one storage means, and the at least one data agent; providing at least one data extractor, for connecting to an existing third-party information system and for interfacing therewith in response to requests processed by the chatbot and the conversational inference module; and, connecting the at least one data extractor to the existing third-party information system. The existing third-party information system may be a medical information system selected from the group comprising physician offices systems, hospital systems, corporate systems, and health care providers network systems. The method may still further comprise the following steps: providing at least one network data agent, operable for connecting at least one preselected physician information system to at least one health care provider network, and further operable for extracting data from the at least one preselected physician information system and providing the data to the at least one health care provider network.

The method may be employed in clustering and visualizing data pertaining to defense intelligence and may further comprising the steps of providing the results of the clustering and visualizing to a human analyst of defense intelligence data.

BRIEF DESCRIPTION OF THE DRAWINGS

The features and advantages of the present invention will become apparent from the following detailed description of a number of exemplary embodiments thereof, taken in conjunction with the accompanying drawings, in which.

DESCRIPTION OF EXEMPLARY EMBODIMENTS

Figure 1:
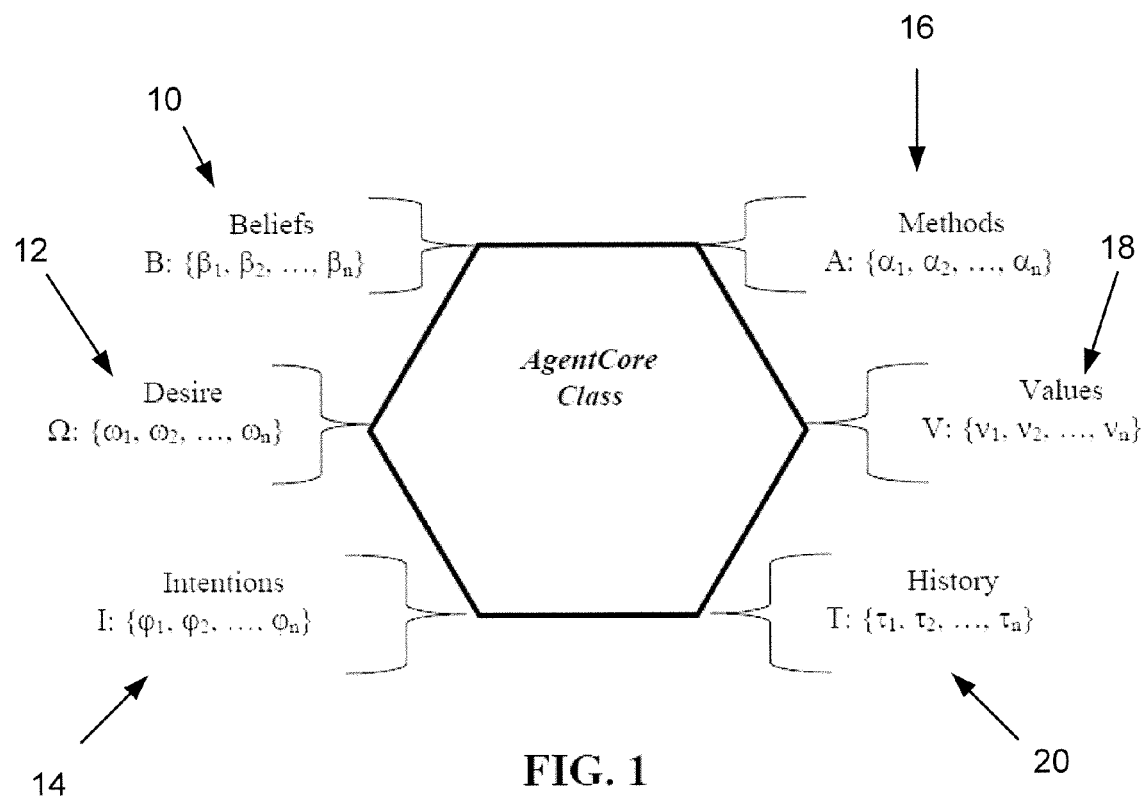
FIG. 1 is a diagram illustrating an idealized Dynamic Molecular Language object in accordance with one embodiment of the present invention.

A solution to the problems described above is presented by the system and method of the present invention, which comprises two key components: Digital Reasoning and Data Bonding. Working together, these two components work with both legacy and contemporary computer systems, learn from software and its users, and translate that learning into increased productivity. Following an overview of these aspects and personal search agent technology, the core of the present invention will be further discussed in detail.

Digital Reasoning Overview

Digital Reasoning synthesizes artificial intelligence technologies for semantic understanding by machines. Digital Reasoning draws from developments in cognitive science, psychology, philosophy of language, and multiple artificial intelligence (AI) approaches. The central differentiator of the Digital Reasoning approach is that it takes an incremental and holistic approach, which ultimately allows software to achieve real intelligence. Rather than attempt to integrate all core aspects of intelligence into the software all at once, Digital Reasoning continually adds new cognitive functions as each function justifies its value in a real business or organizational context. The knowledge representation structure, one of the most critical elements of any strong AI system, is designed to anticipate many of these additions, and is built with scalable understanding in mind. Two significant aspects of Digital Reasoning are artificial intelligence in conjunction with neural networks, and intelligent software agents.

Artificial Intelligence

Artificial Intelligence (AI) is the attempt to simulate human judgment in machines. In a common implementation of AI in a commercial setting, massive amounts of information are filtered into relevant, usable pieces through the use of complex software employing numerous rules. Another approach to machine judgment and learning, Neural Networks, has become a distinct field based on its use of massive parallel processing models to order unstructured information. Yet another approach is the use of advanced statistics, typically referred to as Bayesian Belief Networks or Bayesian Neural Networks, which are used to create unsupervised learning in machines. These approaches make up the core of commercial AI technologies. While AI research has progressed substantially in the past five years with the advent of more powerful hardware, a great deal of the most promising research has yet to be commercially applied. Moreover, there is a pressing need for a way to bring these divergent approaches together to overcome the shortcomings of each individual approach, and to store in a flexible way that mirrors the conceptual structures of the human mind. In summary, most AI approaches allow computers to extrapolate from existing information to make judgments about future events, albeit with only limited success.

This invention presents a new knowledge language, Dynamic Molecular Language, that unites these AI approaches and takes them to a new level. Details of this new knowledge language and its implementation are explained in Appendix A to this application and to U.S. Provisional Application No. 60/382,503, entitled "Knowledge Discovery Agent System and Method," filed May 22, 2002 by Timothy W. Estes, which is a part of this specification, is incorporated herein by reference and is made fully a part hereof. The software implementation of these details is set forth in the CD-ROM accompanying this application which is also a part of this specification, is incorporated herein and is made fully a part hereof.

Intelligent Software Agents

The development of agent software began with the creation of independent task-specific programs, called Bots. Now in widespread use, Bots allow web sites to provide meta-searches, news updates, and comparison-shopping. True software agents are autonomous programs capable of performing multiple duties or tasks. The synthesis of technologies from agent software and AI led to the creation of Intelligent Agents (IA). IAs can make decisions by utilizing some level of deliberation. By learning from the user and the environment, these current approaches to agent technology create intelligent and autonomous action.

Multi-agent systems are among the current research in this area. This technology has extended agent technologies to create community learning and collaboration and has its roots in advanced modeling software and Artificial Life. By assigning rules and behaviors to many small programs, Artificial Life scientists have created simulations of advanced, complex systems such as population growth of certain species in an environment where multiple predators exist. Some current implementations of multi-agent systems utilize a distributed structure that allows them to spread processing and storage over multiple systems, thereby solving problems faster and more efficiently. These distributed intelligent multi-agent systems represent the cutting edge of agent technology today. The present invention adds the advanced agent capacity of intentional agent self-modification to the field of intelligent agents. Such advanced agents are capable of rewriting their own code and changing their own actions as they run. Details of this advanced agent capability and its implementation are presented in Appendix A to this application and to U.S. Provisional Application No. 60/382,503, entitled "Knowledge Discovery Agent System and Method," filed May 22, 2002 by Timothy W. Estes, which is a part of this specification, is incorporated herein by reference and is made fully a part hereof. The software implementation of these details is set forth in the CD-ROM accompanying this application which is also a part of this specification, is incorporated herein and is made fully a part hereof.

Data Bonding Overview

Data Bonding is the process of bringing together data from multiple systems to create collective knowledge and functionality. The goal of Data Bonding is to give businesses and organizations a bridge between systems that are otherwise incompatible Data Bonding uses a combination of existing translation and systems integration technologies and connects them to a core aggregation engine that brings information together upon request. This provides businesses or organizations with functionality similar to having a full data repository without the problems of synchronization and overhead of duplicating all of a business' or organization's data.

At its core, Data Bonding fulfills the role of scalable and flexible businessware. Data Bonding, however, takes this core functionality several steps further by providing integrated knowledge recognition and organization abilities. Moreover, Data Bonding is "business process aware." When implemented in software, it is able to bring improvements to a business or organization's processes as well as enhanced management of its knowledge assets. By creating virtual repositories of knowledge and business processes, Data Bonding can also give managers unprecedented levels of understanding about their business or organization, and allow them to improve efficiency by easily spreading best-of-breed processes throughout the organization or business.

Further details of data bonding and its implementation are presented in Appendix A to this application and to U.S. Provisional Application No. 60/382,503, entitled "Knowledge Discovery Agent System and Method," filed May 22, 2002 by Timothy W. Estes, which is a part of this specification, is incorporated herein by reference and is made fully a part hereof. The software implementation of these details is set forth in the CD-ROM accompanying this application which is also a part of this specification, is incorporated herein and is made fully a part hereof.

Personal Search Agent System Overview

One exemplary implementation of the concepts discussed above and further disclosed in Appendix A and the enclosed CD-ROM is a Personal Search Agent (PSA) which is a multi-phase effort designed to develop a set of search tools using Digital Reasoning and Data Bonding technologies developed by Unetworks. These new search tools learn the users preferences of a user and can infer his or her intent based on environmental factors and learned behaviors. This enhanced insight into the user's preferences, environment, and behavior, provide the user with a concise and better-fitted listing of responses to a given query.

Key features of the PSA, in accordance with one exemplary embodiment of the present invention, include managing selected search engines, learning from the user's behavior, drawing an inference about the user's query to better understand the intent, analyzing the responses collected, building a conceptual network of the knowledge contained in the responses, building a list of categories to allow the user to focus his or her search, presenting responses to the user, monitoring the behavior of the user, and analyzing click stream actions.

By leveraging historical learning, the PSA system can both improve its conceptual understanding of the data and better model user intent. Among the many benefits resulting from this technology are the following: the PSA learns with every search performed, constantly improving its ability to accurately recognize key concepts and rank results; the PSA continually develops a more acute ability to recognize the key concepts underlying the true focus of a user's query, yielding highly personalized results aimed that that particular user's desires; and, the PSA has far richer and more accurate knowledge about given results as compared to conventional search technology, since the conceptual networking capacities of the system focus on the key concepts and concept relationships in the results and continually learns. Moreover, the fact that the PSA continues to learn with every search and from every user gives it far more semantically accurate knowledge.

Further Detail on Core Aspects

A core technology of the present invention is the implementation of Digital Reasoning within a malleable intelligent software agent framework. This technology is derived from conceptual mechanics theory and philosophy. Progress in the actualization of elements of conceptual mechanics theory into coded cognitive models to extend agent systems is the driving force behind the research and development of much of these innovations. Each significant innovation is isolated into a genus that serves as the code base for several different applications to different fields. Two envisioned markets for utilization of the present invention are the Government/Defense Intelligence Market and Health Care Information Systems. One genus of applications of the present invention opens up clear applications in public, corporate, personal, and educational information systems.

Dynamic Molecular Language (DML)

DML is a cornerstone concept according to various embodiments of the present invention, which aims to create a transportable "core" or "brain" of an agent that carries within it all of the essential elements to constitute an agent at a remote location. DML goes beyond the idea of standard distributed object technologies because it treats cognitive elements (i.e., knowledge representation, plans, sensors, and the like) as distributed data objects. While component cognitive distribution may involve some conventional aspects (distributed AI and multi-agent systems have shared the idea that intelligence emerges from distributed learning structures), DML objects are not agents. In old philosophical parlance, they are the individual "essences" of agents, and DML is meant to be the ultimate framework within which agents operate and are transported. Succinctly put, if an agent is a finite state machine, then DML is short hand for the complete state space of the agent that is interpretable by the system. It is therefore analyzable independently from individual agents and creates a continuum of experience for agents of a DML system.

With reference now to FIG. 1, from an implementation standpoint, DML is essentially a hybrid data structure containing six primitive element types: Beliefs 10, Desires 12, Intentions 14, Methods 16, Values 18, and History 20. This is a somewhat extended version of standard Belief, Desire, Intention (BDI) models of agents. The additional primitives are meant to add the following features: Methods 16—these are the executable modules of the agent that extend an AgentCore class with required functionality for that agents' purpose; Values 18—these are global limit parameters or "codes of conduct" that are set within the execution environment of a local system or transmitted to an agent prior to its being moved to a foreign execution environment; History 20—the history primitive contains a vector of previous attempted plans (Intentions in this model), the belief state of that plan, as well as methods invoked by that plan.

The History 20 primitive is the major extension to the BDI framework because it opens the possibility of substantial recursive definition of patterns of action within the system as well as deviation analysis from the ideal end state vector (the satisfaction of the Desire). Desire(s) 12 can be either a single desire or an ordered set by priority that could be subsumed into the label of the set of desires. There is also a further decomposition of the "primitives" possible by looking at them at a computational level as atomic actions (the elements of an Intention 14-Methods 16) and their parameters (Beliefs 10). This opens up the idea of an "ultra-primitive" binary transformation space for all possible agent actions (though at this level the conceptual aspects of what the agents are doing would be nearly impossible to categorize). Whatever the appropriate primitive level, at this early stage there is an implicit spatial metaphor going on that anticipated the later formalizations of conceptual mechanics theory. There are numerous other features and aspects of this data structure (such as which parts are mutable by the agent and which ones represent true constraints, the further interdefinability of primitives reducing the absolute range of unique identifiers, etc.).

Organic Software Agents

The idea of using a Society of Agents to model the social emergence of meaning is a very popular idea in cognitive linguistics, and one model was well popularized in Marvin Minsky's *Society of the Mind*. Technologically, this has been a lot easier said than done. Collective learning and decision making (whether it be in cooperative or competitive agent models) is relatively straightforward with static or simple reactive agents as primitives in the system. Doing the modeling with complex, learning agents (which is the true desired model) is many orders of magnitude more difficult; intentionally malleable mobile network code is a completely new area.

Organic Software Agents (OSAs) are software agents having the capacity for intentional self-modification based on cognitive judgments. They can essentially choose what types of methods they will need based on the situation they encounter and then dynamically extend their AgentCore to use the new code. In some sense, every learning agent is intentionally modifying its belief state every time it encounters new stimuli that might alter its belief state. The OSA model is to extend this capacity to cover its methods, not just the parameters passed to those methods. In a sense, OSAs consist of programs with fixed cognitive capacities (sense, perception, learning, inference, etc.) and variable functionality with coupled parameter ranges.

From an application standpoint, there are strong implications. An OSA with person-specific intelligence may dynamically create applications by assembling the appropriate component objects. A real world example of this would be outfitting a Common Business Object package with OSAs that could judge what particular applications are needed for each individual within a business and assemble those applications on demand. There are also straightforward applications to web-services and distributed computing systems by using OSAs as intelligent service brokers and mediators. In many ways, the OSA idea presupposes solutions in critical areas.

Dynamic Conceptual Network (DCN)

A critical need in knowledge representation is striking a balance between fluidity, structure, priority, and compression. Many symbolic approaches are sufficient to capture priority and the structure of knowledge in fixed contexts.

Artificial Neural Networks (ANNs) are adept at the recognition of patterns and non-monotonic inference due to their highly parallel processing structure. This allows them to capture a lot of the fluidity of inference in human mental processing. Particularly, ANNs (if they are created with sufficient size and richness) can isolate relational connections that are not representable symbolically. ANNs, however, are extremely processing and memory resource intensive and keep a great deal of redundant information in their high-granularity structures. Another drawback of ANNs is their inscrutable or "black-box" nature, which makes observation and renovation of their learning very difficult.

With these drawbacks in mind, the design of the knowledge representation structure of the present invention was made to have dynamics similar to ANNs (particularly for cross-context inference), but structured and rapidly executable within a context. Taking a page from semiotics, it centers on super-symbolic theoretical structures (concepts) bound along certain activation paths from other concepts. These activation paths are "relationships" that bind particular concepts within a conceptual continuum. The activated subset of the conceptual continuum is denoted as the context.

The following is a step-by-step example approach. First, there is the pattern input (the feature detection level of the system) where the stimuli enter into the system through a process of "discretization." Discretization takes a given perceptual chuck—which at the data level could be a sentence in a text document (unstructured source) or a table in a database (structured source)—and tokenizes and parses it into discrete feature dimensions. The pattern input level is, therefore, a highly modular level that could go from NLP elements to visual sensors with neural-network based pattern recognition capacities. The important element of this level is not the sensors, but the ability of the sensors to appropriately classify the varied input into primitive dimensions or finite ranges in feature spaces. An example of this would be the ability of a NLP parser to accurately perform part of speech analysis and per-sentence and per-word tokenization. The various parts of speech may be mapped to discrete points along a "grammatical axis" with the particular words along a "vocabulary axis" from the systems' memory. While a binary dimensional representation is not very interesting in itself, a sufficiently rich hyperspace of "n" axes with historical learning encoded compressed into other axes is. As a side note, there is anticipation of the spatial notions in conceptual mechanics theory, and it should be pointed out that the axes relevant for a particular analysis are not limited to reorganizations of the limited "simple" encoding of the stimuli but may also involve the plotting of more "complex" dimensions that are compressed forms of previous observed patterns.

Figure 2:
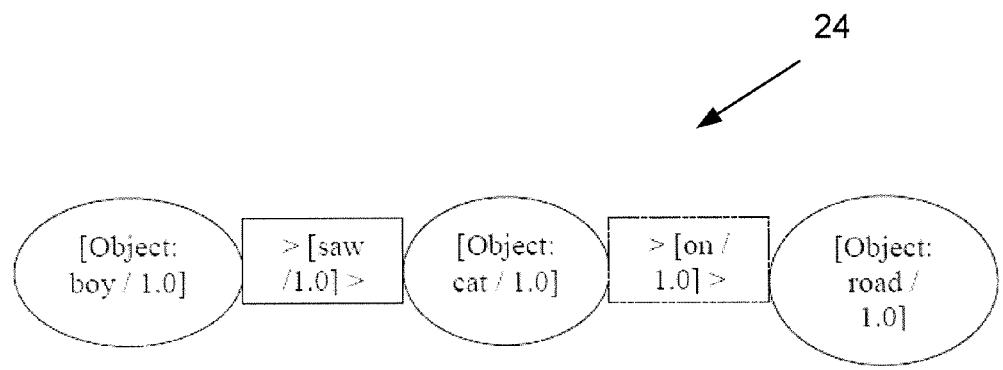
FIG. 2 is a diagram illustrating a feature map according to one aspect of Dynamic Conceptual Networks in accordance with an embodiment of the present invention.

Laying down this schematization creates a kind of dual feature map—one map is the connections within the chuck (features automatically correlated simply because they occur in the same chuck), the other is the features of the chuck discretized as coordinates within the hypothetical feature hyperspace. FIG. 2 is an illustrative diagram 24 of an ideal map of the first kind taken from the following parsed sentence:

Sentence: The boy saw a cat on the road.

Part of speech tagging: [<article/ the>, <nounSubject/ boy>, <verbPrimary/ saw>, <article/ a>, <nounObject/ cat>, <Prep/ on>, <article/ the>, <PrepObjectNoun/ road>]

Figure 3:
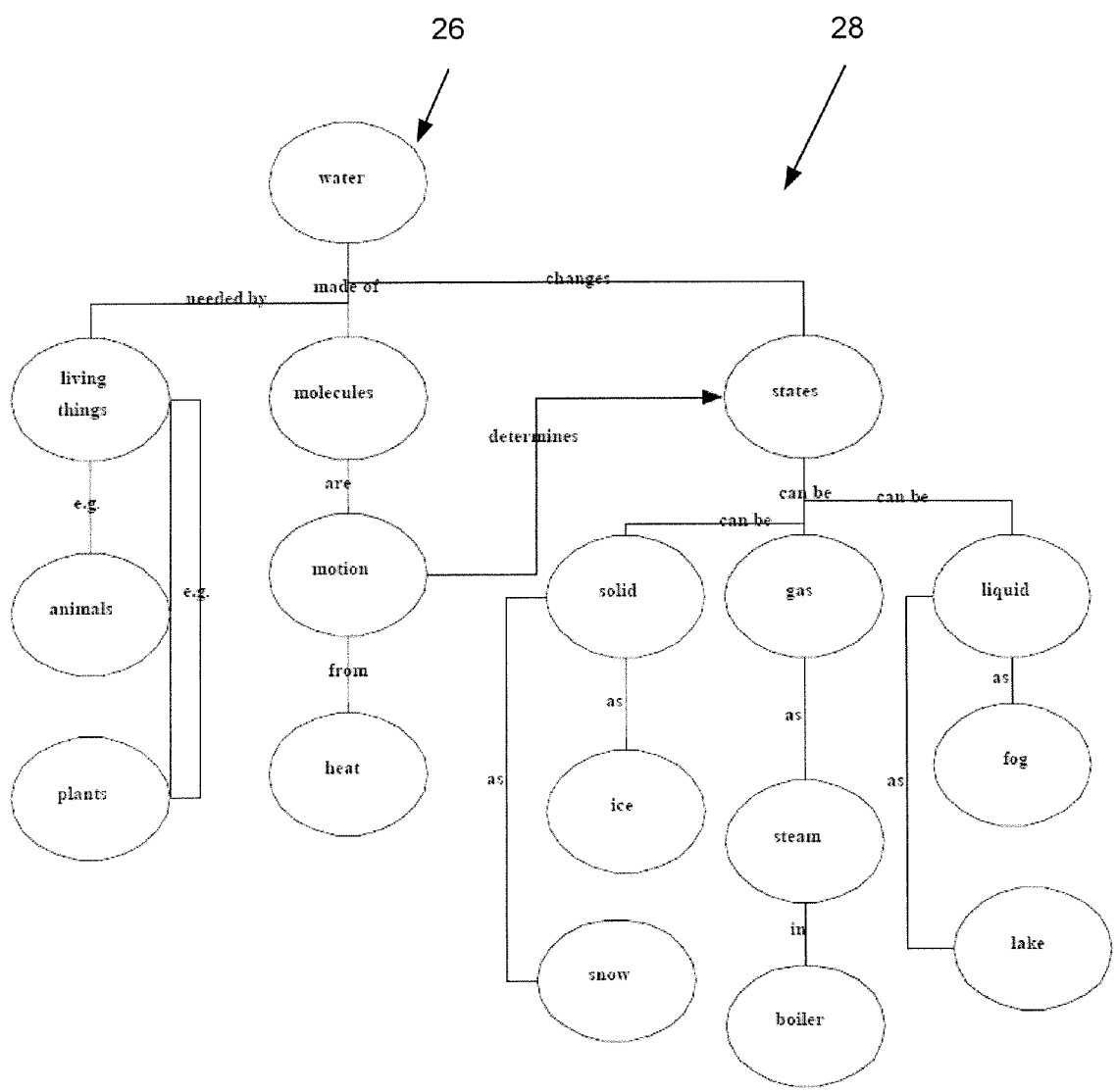
FIG. 3 is a diagram of a concept map illustrating another aspect of Dynamic Conceptual Networks in accordance with an embodiment of the present invention.

What is given at the end is strikingly like a very small semantic network representation or even a conceptual graph. There are weight factors in the example, but they are non-informative for a single instance. This representation is a single sentence, basic conceptual network. A conceptual network is distinct from a semantic network in that it is acquired dynamically. Of course, this system is a static conceptual network and therefore would function like a standard semantic network in inference, comparison, and recognition analyses. A dynamic conceptual network (DCN) is not just learned, but obtains its residual structure from the second type of feature map discussed earlier. A mature, learned concept ("water" 26 in the example) may easily take a shape similar to the "concept map" 28 shown in FIG. 3. Concept maps are borne out of research by Roger Gowin and others in applied psychology working on improving education to children. They are nearly always static devices, much like diagramming a sentence, and which can be formalized into semantic net like structures fairly readily. As a symbolic knowledge representation scheme, Sowa's concept graphs are considered the preferred symbolic output standard for the description of the present invention.

A couple of key distinctions are that the relationship bindings and concept labels have a weight on them, giving them a somewhat ANN-like structure. The weights may be adjusted by an algorithm that takes into account the different feature dimensions and the values passed for them by the feature detectors. The DCN then is a dynamical system of symbol experience (under the assumption that it was the only experience encountered by the system such as in a NLP application) that creates emergent attractors with labels and first-order node links. The DCN, when stored, is like a flat graph where every potential relationship can be seen as an edge and every concept as a vertex. The weights and their schematization into dimensions, however, dynamically create a highly granulated and meaningfully ordered state-space along all projected feature ranges. This graph, the DCN, is therefore a compressed, potential hyperspace that encapsulates a full continuum of concepts both experienced and possible.

Development and Fields of Application

The software system of the present invention utilizes Java™ language, because of its widespread acceptance, portability, and its extensive use in enterprise systems. With the consideration that the present invention required a highly stable and robust platform that could handle essential services for web-based and distributed software development and deployment, development was done on the Java™ 2 Enterprise Edition (J2EE) platform technologies using a Java Beans™ component software model.

A key market opportunity for the software is in the automation of knowledge creation or "knowledge integration" and making that as accessible as possible to the end user. This entails that the greatest need for products utilizing the present invention will be where there is the greatest "dis-integration" of knowledge. This may be at the enterprise level, particularly in enterprises where there are multiple heterogeneous systems with a combination of structured and unstructured information in multiple formats. Thus, the technology of the present invention can be aimed at applications in the Government and Health Care industry. While these are very difficult "problem spaces," they have the most acute need and therefore are ideal spaces to justify a rapid and substantial return on investment.

Personal Search Agent System (PSA)

One embodiment of the present invention which may serve as a strong stand alone application and proves the world-use-utility of the DCN structure is called the Personal Search Agent System (PSA). The personal search agent system is a thin-client, fat-server J2EE application designed to provide user-personalized Internet search aggregation, filtering, and presentation. Succinctly, it is an intranet-deployable learning search engine targeted at large organizations. Among the data sources supported are HTML and XML. The PSA is composed of several agents that work together to collect the data, filter it, and present it to the end user of the system.

Functionality of the PSA

The PSA is designed to address problems that arise from using conventional search techniques and tools. A person who wants to find a website, document, or is just searching for information on the Internet generally uses a search engine. Several search engines exist to support the user and provide them with an extensive list of results to the query. The problem, however, is that the results returned are not necessarily supportive of the user. These results suffer from some of the following drawbacks: they are very long; they does not always meet the expectation of the requester; they are not aligned with the intentions and/or needs of the request; they cross many conceptual planes; they expect the user to sift through hundreds or thousands of potential addresses with little understanding of what the respective site contains; and, they may not be appropriate (i.e. accidentally accessing inappropriate sites). To address these problems, the PSA learns the user's preferences and may infer the intent of the user given environmental factors and learned behaviors. This enhanced insight into the user's preferences, environment, and behavior, provide the user with a, concise, and better-fitted listing of responses to a query. This tool is composed of a group of agents that perform many tasks, including but not limited to: managing the selected search engines; learning from the user's behavior; drawing an inference about the user's query to better understand the intent; analyzing the responses collected; building a conceptual network of the knowledge contained in the responses; building a list of categories so the user can focus his/her search; presenting the responses to the user; monitoring the user's behavior; and analyzing click stream actions.

The following is a storyboard presentation of how PSA works from a user's point of view. The PSA is designed to have the following user interface—a "file folder" web page user interface. The following storyboard details the web page user interface:

Web Page User Interface
1. The user opens the query input interface.
2. The UA presents the query input page.
3. The user inputs the keyword(s) for the query making a query statement.
4. The UA offers category options that may be included in the query statement.
5. The UA offers Boolean options to better refine the query statement.
6. The user submits the query.
7. The UA formats the query statement, adds the users identification, and forwards it to the server-based agents for processing.
8. The system submits the responses, current list of categories, and the link to the subset of response that are associated with the category to the UA.
9. The UA presents the user with a split screen page.
10. The user sees a list of categories on one part of the split screen page and a complete listing of responses on the other.
11. The user may select a listing from the compiled list and go immediately to the source.
12. Alternatively, the user may select a category.
13. The UA then presents the user with the subset list of responses associated with the selected category
14. The user may then select a listing from the compiled list and go immediately to the source.
15. The user may select a different category and steps 13 & 14 repeat.
16. The UA collects all user actions taken within the split screen page.
17. The UA reports all user interactions (behavior) to the system.
18. The system updates the user understanding based on the interactions report.
19. The UA may also offer the user a survey form to complete which collects the user's feelings and reactions about the search session just completed
20. The users completes the survey
21. The UA reports the survey data to the system to update the system's understanding about the user's preferences and intent.

To summarize, one embodiment of the PSA of the present invention contains the following core functionality that is of substantial value to particular industries and is of critical importance to all future agent systems: mining of user habits and association with related concepts; concept-based clustering from document content; and, continual concept refinement from historical learning.

Architecture of the PSA

Figure 4:
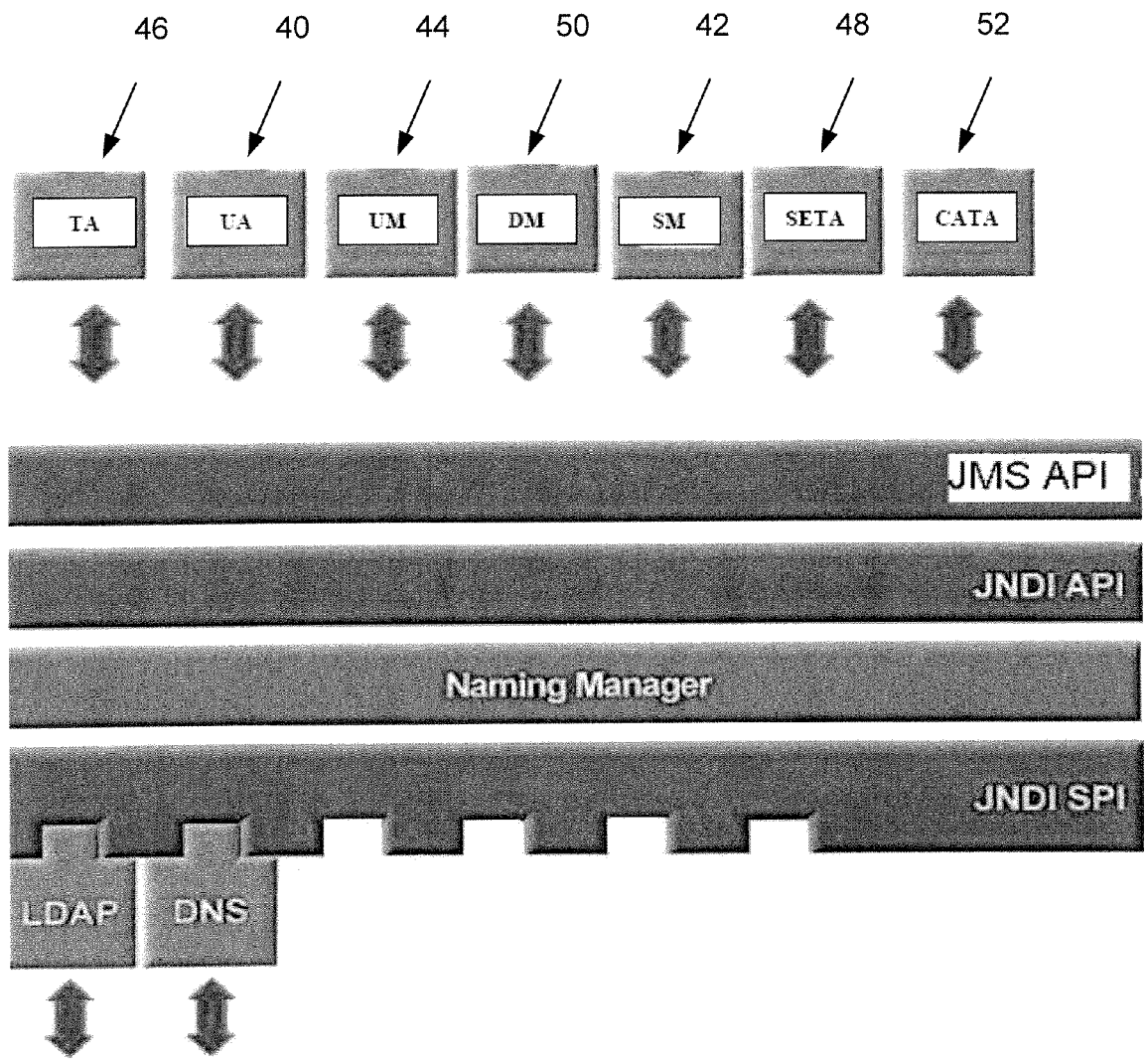
FIG. 4 is a diagram illustrating the architecture of the Personal Search Agent system including each of the task-specific agents composing the multi-agent system in accordance with an embodiment of the present invention.

With reference now to FIG. 4, the architecture of one embodiment of the PSA is a multi-agent system composed of Enterprise Java Beans that execute within a common EJB container subscribing to J2EE services that support the messaging and naming services for the agents. Within the PSA, each particular agent takes a piece of the workload and sends messages to coordinate with the other agents. The PSA uses the Java Messaging Service (JMS) as its primary messaging service because it allows easy transportability of objects as messages, thereby giving the agents to pass data and methods. The capacities of the different agents are as follows:

User Agent (UA): The UA 40 is responsible for two functions. The primary function is to manage the presentation to the user. The secondary function is to provide information on user actions to the User Miner module.

Search Manager (SM): The SM 42 assigns tasks to the search engine task agents (SETAs). It collects the results, removes duplicates, validates the links, and orders the responses.

User Miner (UM): The UM 44 is an agent that passively learns the behavior and preferences of the user. Based on the performance of the user over time, the UM provides information used to analyze both the query statement and results.

Task Agents (TAs): Task agents 46 are single function programs that are looked at by the system as other agents. The most common TA in this project is the interface TA.

Search Engine Task Agents (SETAs): The first phase of the PSA develops several SETAs 48. Each SETA is able to interoperate with their specific search engine. They contain the ability to submit a properly formatted query to the search engine and then receive the response.

Data Miner (DM): The DM 50 is an agent similar to the UM 44. It learns from the responses and builds the conceptual map of the topic. The main functions of the DM are to analyze the response, key meta-information about each response listing, and select pages associated with each individual listing. Analytics for the PSA will include: 1) Concept Analysis—the numbers of time a concept is referenced in relation to a query term; and 2) Concept Links—number of times related concept show up relative to a set of concepts in a meaningful relationship.

Categorizing Agent (CATA): The CATA 52 analyzes the response and looks at the conceptual mapping of the listed items. It then determines potential categories based on the systems configured parameters such as the top N concepts and concept links or top N percentage of concepts and concept link.

Knowledge Acquisition in the PSA

Knowledge Acquisition in the PSA occurs through the tokenization and parsing of unstructured sources and processing of those data into schema for the DCN of the present invention. The NLP elements of the system can be Java Beans, such that document parsing and tokenization (which can be resource intensive once 1000+ documents are being processed, for example) could be done through a distributed algorithm. Once given documents are parsed, tokenized, and the key elements are tagged according to the present invention, the DM begins to analyze the results. In one embodiment, the PSA is primarily concerned with learning associations between key concepts. Thus, the PSA extracts key concept words e.g. nouns, adjectives, combinations, proper names, etc., that co-occur within a sentence, which are taken to be a semantic unit. The concepts and their concept links, i.e. concepts that co-occur with them in the same sentence, are catalogued and sorted into a concept network that represents that structure. As an example, the example sentence appearing supra, "The boy saw a cat on the road," would create the following concepts and concept links: Boy-cat, cat-road, boy-road.

In one embodiment, therefore, the PSA acquires essentially an array of concepts formatted in such a way as to be mathematically interchangeable with a weighted, undirected graph. At a per-sentence level, this functions as an intentionally compressed representation. At a document or document-set level, this can create an extremely meaningful indexing system without requiring any human intervention.

Knowledge Representation in the PSA

As stated supra, the knowledge acquired from unstructured sources is somewhat simple, yet it can yield impressive results when applied over a large document set. As the concept network—static in every act of acquisition—becomes more complex, emergence of meaningful attractors in the concept-concept link tuple set are made more possible. This same effect can be achieved by continued exposure of the PSA to new documents over time, and in this way the concept network may finally become significantly dynamic.

Figure 6:
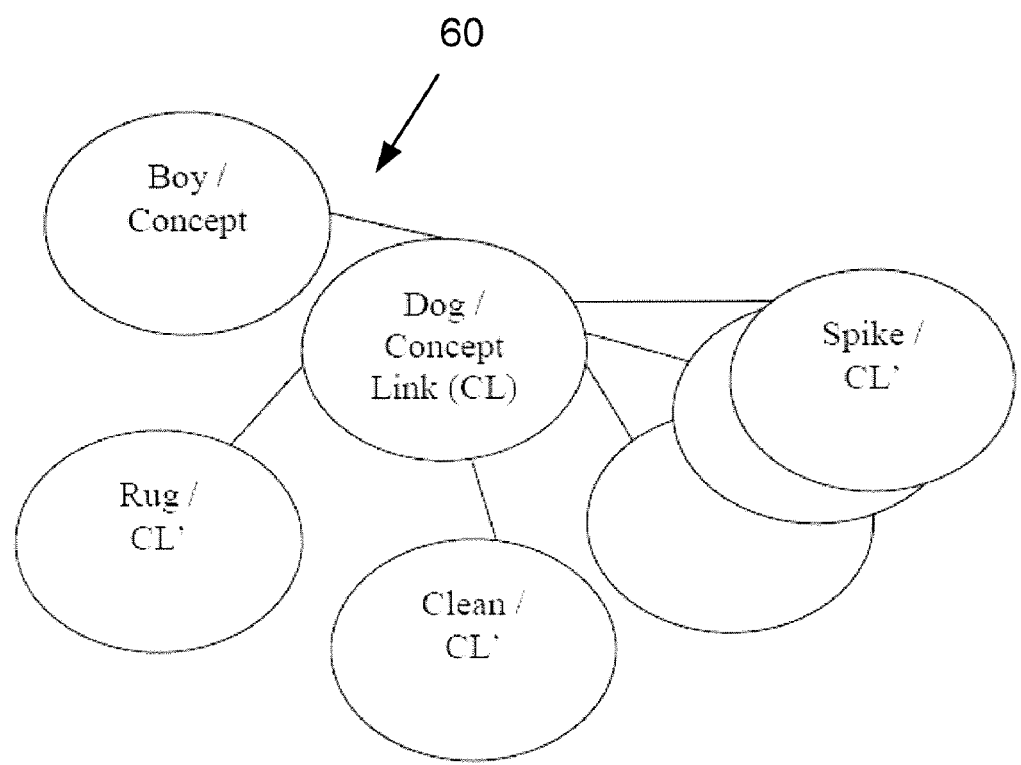
FIG. 6 is a diagram of a concept network illustrating one embodiment of the present invention.

Following from the above example, in a large document set where the discussion features a boy and his dog, the boy-dog tuple 60 may become a focus of many other aspects. FIG. 6 shows an example of links that may be generated.

Now, in an actual conceptual network embodiment according to the present invention, each link may be weighted proportionate to the others. In addition, each one of the terminal nodes may have links to the source document(s) in which the concept—concept link—$2^{nd}$ order concept link occurred. Further, the search may go to the $n^{th}$ order link binding from the stored DCN; however, at some level noise may render the less meaningful. Indeed, a novel aspect of the present invention is that while there exist n-number of possible search paths, those paths are optimized automatically based on meaningfully linked items, from the human's perspective and not the machines'. In fact, a type of associative inference can proceed up and down the network—there exists hierarchy, but no fixed hierarchy—instantiating new trees based on new streams of relations. This effect can be analogized to pulling up on a rubber sheet, in that everything can organize around the point on the sheet that one pulls on; similarly, isolating a focus concept in the DCN organizes all the discovered concepts around this concept.

User-Driven Learning of the PSA

As yet another aspect of the PSA according to the present invention, it may observe the way humans utilized its generated results by tracking click stream data in the UI. Thus, it can learn from what a user does without changing the way a user searches or requiring additional effort for ranking or questionnaires. As an example, if a query with its key concepts causes the user to select documents 4, 6, and 11, the PSA can look at the concept network of that document and compare it with the first-order node links of the queried concept, and then adjust the weights accordingly. This may be done in a waterfall fashion, with the strongest effects occurring to that particular user's profile, then her work group, then the entire DCN that she is connected to. These habits can also be used to create affinity groups based on similarities in users' top-level concepts in their own weighed concept network.

Conceptual mechanics philosophy holds that intentionality is a necessary condition for intelligence. Since agents do not have any innate intentionality, it must be donated or seeded by humans who create them. In a sense, every program is a little, tiny piece of human intentionality broken off and translated into a Turing-computable form. The PSA of the present invention represents a start to programs that deliberately capture that intentionality and in so doing create a reference point from which to translate mathematically meaningful schema into humanly meaningful schema. While formal logic has shown there to be great overlap between the two, they are not coextensive. In logic everything is explicit, while in human thought and human language, most knowledge is implicit and cannot be retrieved through monotonic transforms.

In summary, the following are some key aspects of the PSA system according to one embodiment of the present invention. First, PSA was designed to deal with unstructured information sources and to cluster them in meaningful ways, and to improve the accuracy and relevance of their clustering abilities with every use. The PSA creates emergent categories from the document sets and natural categories over a long period of historical learning. Thus, the PSA dynamically generates simple associative ontologies which are themselves dynamic. In addition, by learning from users, the system of the present invention can normalize on human semantics at the high-associative level.

Second Generation Dynamic Conceptual Network (DCN2)

A second generation of the Dynamic Conceptual Network (DCN2) of the present invention expands in three areas: granularity of acquired and stored knowledge, compression of knowledge representation, and vastly richer inference mechanism. As alluded to in earlier sections, both DML and DCN ideas presuppose a continuous conceptual hyperspace where there are intelligible and discrete dimensions. In fact, to connect these two most fundamental ideas requires seeing the DCN as the knowledge representation structure of the belief states within the DML object structure. The DCN provides both the array structure and the dynamics for array transformation that are necessary to maximally conserve processing time and storage space for belief state dynamics.

It can be assumed that the other state-spaces isolated within the primitives of the DML object will have similar high-level dynamics (i.e. methods can be associated to the belief state by the fact that they perform changes on environment parameters, agent belief states, system belief states, etc.). Values differ slightly, because they merely limit the range of acceptable parameters passed to certain demarcated functions (they can therefore be operation limits, environmental limits, or ethical limits). Desires are end state vectors for the agent (they therefore must be definable or interpolated between pre-experienced ranges). Desires are satisfied by particular series of possible Intentions (more than one series may satisfy, and more than one sequence of the same set may satisfy). Intentions are plans or strategies that are composed of a sequence of methods with appropriate belief parameters passed so as to modify the state of the agent or its environment. Definition-ally, the proper sequence of methods and beliefs is all that is necessary for any agent to accomplish its desire.

Formally, the primitives are inter-definable in the following ways:

$$(1) S(\Omega) = \sum_{i=1}^{n} S(\omega_i)$$

Decomposition of Desire into Desires $$(2) \sum_{i=1}^{n} S(\omega_i) = \sum_{i=1}^{n} (\varphi_i)$$

Decomposition of Desires $$(3) \sum_{i=1}^{n} (\varphi_i) = \sum_{i=1}^{n} \sum_{j=1}^{n} [\alpha_i(\beta_j)]$$

Decomposition of Intentions $$(4) \text{Dfn } \alpha := \alpha(\beta_x) = \beta_y$$

Definition of a method where S(x)="x is satisfied." Given (4), it follows that all changes in agent state space can be modeled as belief changes. This is a rather remarkable fact because it means that if a working algorithm can be found to give substantial depth and fluidity to the representation of knowledge in an agent, then it may be extended to give the agent reflexive understanding of its own agency (in terms of its capacities, both actual and potential beliefs, and its state within its environment). In this way, the epistemology of software agents creates a world that is solipsistic. This can be seen as a straightforward corollary of every aspect of a software agent existing in a formal system.

The dynamics of belief states and the dynamics of methods will be formally identical, but the dimensional structure will be very different. After all, belief states are derived from features experienced by the agents and methods are transformations of experienced features. This is where concepts, modifiers, and relationships reenter the picture. Concepts are stable symbols (functioning as a type of attractor) that are tied consistently to certain ranges of multiple feature spaces. Modifiers are stable symbols that consistently change the prototype of a concept by altering, adding, or subtracting feature(s) of the concept. Relationships (or predicates) are a projection cone of allowable transformation for part or all of the belief state that it operates on. This is basically comparable to "pruning" whole types of leaves from a tree in a heuristic search of a state space. Further, there is competition going on that is similar to some types of recurrent ANNs; as sufficient features are detected, whole concepts are activated and other "invisible" features are inferred while at the same time, counteracting this rapid expansion in state space, relationships "target" the expansion and modifiers limit the range within particular feature-space dimensions. This accurately "frames" perception and closes the belief state into a manageable form.

To address another end of these issues, conceptual mechanics theory suggests that the state "space" should be taken as literally as possible in representation. This means that every feature dimension should have to be dynamically scaled, with its units (which in many cases will be symbols such as words) turned into a continuous number line. A hash table, therefore, should be attached to each dimension with the (symbol):(numerical range) correspondences to translate it back into a scrutable structure. With this encoding, perception, memory, and inference should all be straightforward vector transformations. Through this model, an example of "$2^{nd}$ order" reasoning is the monitoring of derivatives of functions of change in particular features of a concept, to seek out deterministic changes which can be remembered (within a compression of the History space and a consequent optimization of all relevant Intentions). In this context $2^{nd}$ order reasoning is reasoning "about" conventional reasoning functions (inference, perception, etc.). From the computational perspective, higher order reasoning (in this model) is merely compression and optimization, i.e. correlated to end states that are meaningful to human beings.

Concepts and their dynamics, when seen in the above purely spatial way, take on "behaviors" and "motion" that are quite reminiscent of quantum particles. Indeed, for "true" inference, a nearly infinite set of possible states should be processed in parallel and transformed into the new set of possible states. There is a "superposition-like" richness in feature granularity (both potential and actual) that is lost by compressing dimensions to optimize inferences. An application of statistical mechanics techniques to these state spaces may create promising ways to correlate macro-level "contexts" with ranges of feature vectors.

DCN2 Knowledge Acquisition and Representation

The following describes the DCN2 algorithm for knowledge acquisition and representation according to the present invention. In the original DCN the algorithm is a basic associative learning algorithm using carefully selected semantic elements. The DCN picks up on concept-concept links by acquiring selected concepts within a sentence such that the data structure for such an object is:

[Concept]-(Associative Weight)-[ConceptLink]

The emergent network structure is a sorted array:

$$\left\{ \begin{array}{c} [\text{Concept}] - (\text{Associative Weight}_1) - [\textit{ConceptLink}_1] \\ [\text{Concept}] - (\text{Associative Weight}_2) - [\textit{ConceptLink}_2] \\ \ldots \\ [\text{Concept}] - (\text{Associative Weight}_n) - [\textit{ConceptLink}_n] \end{array} \right\}$$

This network creates interesting "deepening" when Concept-Concept Link tuples begin to "pile on top of each other." As a result, there is rudimentary reinforcement learning with a network learning effect. The learning occurs in localized regions of the concept network and alters the global topology of the concept network gradually. If this were presented visually, there would be an emergent topology of concepts. The isolation of one concept, as is the case in a query, would yield a particular "slice" of the surface and the linked sources.

The DCN2 supplements this area by adding an Augmented Language Processing Module (ALP), an Agent Memory Module (AMM), and an Agent Inference Module (AIM). The ALP is the specific module that deals with knowledge acquisition from unstructured information sources. The ALP can work with the NLP parsing tools in Inxight's LinguistX™ Platform SDK to apply a set of heuristics, to make approximate guesses as to the semantic roles of various words that occur in a stream of text. The primitive semantic roles are that of Subject, Predicate, and Object. In addition, there is a role of Modifier that can apply directionally toward any of the other primitives, or the entire semantic unit. An example of the above primitives in use would be as follows:

Subject (S): {noun, pronoun, etc.}
Predicate (P): {verb, etc.}
Object (O): {noun, etc.}
Modifier (M): {adjectives, adverbs, etc.}

Figure 5:
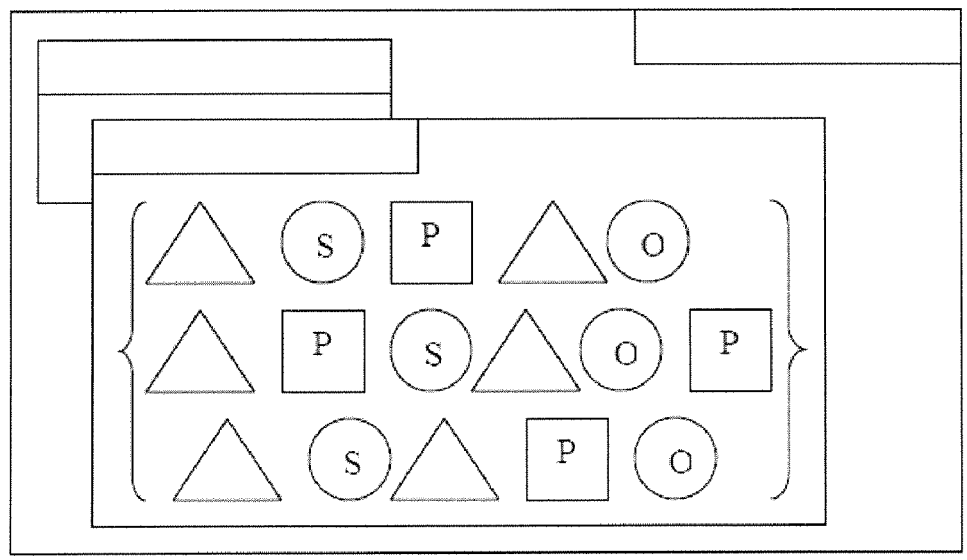
FIG. 5 is a diagram representing a graph structure created by the Augmented Language Processing Module of the second generation Dynamic Conceptual Network in processing a document in accordance with an embodiment of the present invention.

The typical form of a processed sentence appears like "MMSMPMMO." A semantic unit is stored as a directed graph structure, a paragraph as an array of graphs in sequence, and a document as an array of arrays. FIG. 5 illustrates a graph structure 58 created by the ALP when it processes a document.

From a data structure level, the ALP returns a value tuple for each of the recognized primitive semantic roles that fills out an ordered array for each paragraph that is nested within the entire array for the document. This allows for a document semantic model to be developed from the data testing for logically consistent relationships and connecting appropriate antecedents where each sentence is not sufficiently explicit. An example of this is the use of pronouns in a few sentences in a paragraph. The pronoun can easily be classified as a concept, but the concept of that particular pronoun string is not particularly interesting over historical periods, as its related concepts would be so diffuse as to not develop any peculiar topology. The pronoun acts like a formal parameter in a logical operation, where it has no particular interpretation until it is coupled to a set of extensions. In the case of the pronoun, this interpretation is likely bound very "locally" i.e. in the previous sentence or within the same paragraph. This exemplifies why it is very important to frame the different levels of analysis to create consistent semantics. A delicate balance must be reached to set some levels a priori and allow others to emerge through experience. Within the ALP, the general representation of the analyzed document is in the form of a table 66 having at least the elements illustrated in FIG. 8.

Figures 7, 8:
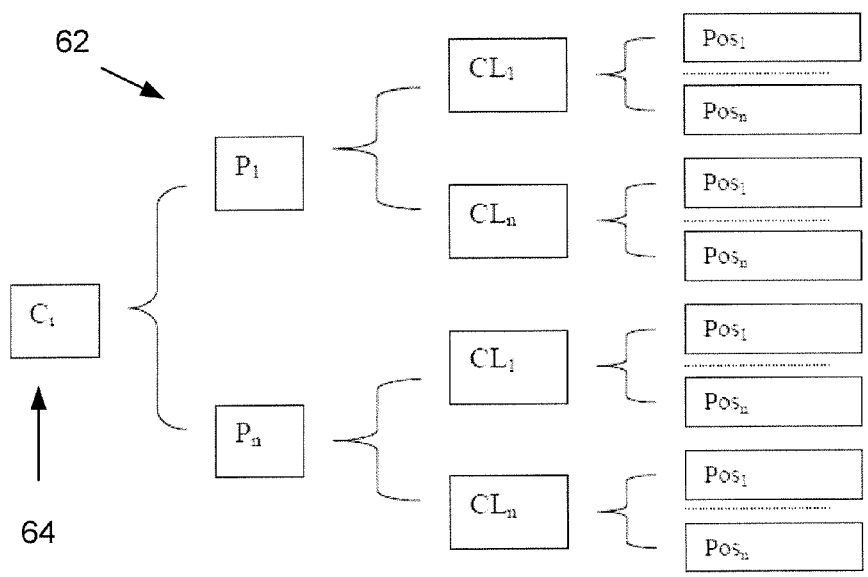
FIG. 7 is a diagram in the form of a concept-focused tree illustrating an aspect of knowledge acquisition and representation in the second generation Dynamic Conceptual Network in accordance with an embodiment of the present invention.
FIG. 8 is a table illustrating another aspect of the second generation Dynamic Conceptual Network in accordance with an embodiment of the present invention.

From these elements, the entire graph structure of earlier can be reconstructed in multiple ways. First, the document can be reconstructed from the standpoint of the clustering about a particular concept, a particular predicate, a particular semantic unit, or even modifiers. A concept-focused tree 62 is shown in FIG. 7. The tree is taken from the $i^{th}$ concept 64 and every branch has n links based on the number of links to that particular element within the document. This graph is not weighted because it makes use of unique position identifier (position within a given document referenced by a URL), therefore guaranteeing that no two branches will be the same. The entire DCN2 can be represented by this same tree, but with a weighted graph having the positions replaced by the URL. The weighting of the DCN2 can be by the total number of occurrences of the semantic unit across its entire range of experience. Other weightings are easily obtained by calculations across the long-term memory of the DCN2.

Compression of Knowledge Representation

A cursory look at the representation structure within the ALP reveals that the storage of the analysis is likely to be the same or greater in size than the original document. Given that the application of this software is to read gigabytes of text (potentially terabytes over a given DCN2's lifespan), an efficient long-term storage structure (a subset of which could be run in memory for fast cognition) design is a critical issue in the DCN2. The Agent Memory Module (AMM) uses economical primitives and heavily recursive "unfolding" of relationships vs. complete storage of relationships.

Figure 9:
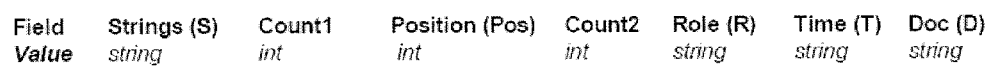
FIG. 9 is a table illustrating yet another aspect of the second generation Dynamic Conceptual Network in accordance with an embodiment of the present invention.

The AMM has many levels of memory based on the particular context of application the AMM's mid-term memory works under the premise that essentially what the ALP is dealing with at a data level is sequences of strings, URLs, and positions within that URL. Since there are a limited number of roles that a given string can take (subject, predicate, object, modifier), these different roles are turned into a value in a "role" field. The initial AMM table structure 70 is as shown in FIG. 9.

Each time a string occurs and is recognized by the ALP, it is stored with its role by the AMM. When it reoccurs, Count1 is iterated (Count1 is the total number of occurrences of the string in the DCN2's history) and Count 2 is iterated for the particular role (Count2 is the total number of occurrences of the string used in that particular role). Finally, an additional entry is made under the subsection of the string and the role adding the position of the string in terms of the data sources it occurs in (URL) and where it occurs in that data sources (integer value from ALP). Under these conditions, Strings (S) grows at an exponential rate initially and then hits an asymptotic value where it ceases to grow appreciable (probably once it has encountered about 400,000-500,000 words which is the likely English vocabulary of 99.9% of the Internet). The counts will scale 1:1 with S. So, four of the five fields are well under control. Those fields should scale to approximately 10-20 MB uncompressed. The fifth field, however, blows up. Position (P) and Time (T) scale linearly with every document based on each document's size. If a normal document had approximately 300 semantic roles, then 300 integers and two strings (one for Time (T), one for the Doc (D)) are generated for every document that is encountered. If 20 million documents were read, then approximately 6 billion integers are added to the table (even though those integers would all likely be in the range of 1-1000). This is very expensive from a storage standpoint, and therefore it is apparent that some type of optimization or compression is needed.

Figure 10:
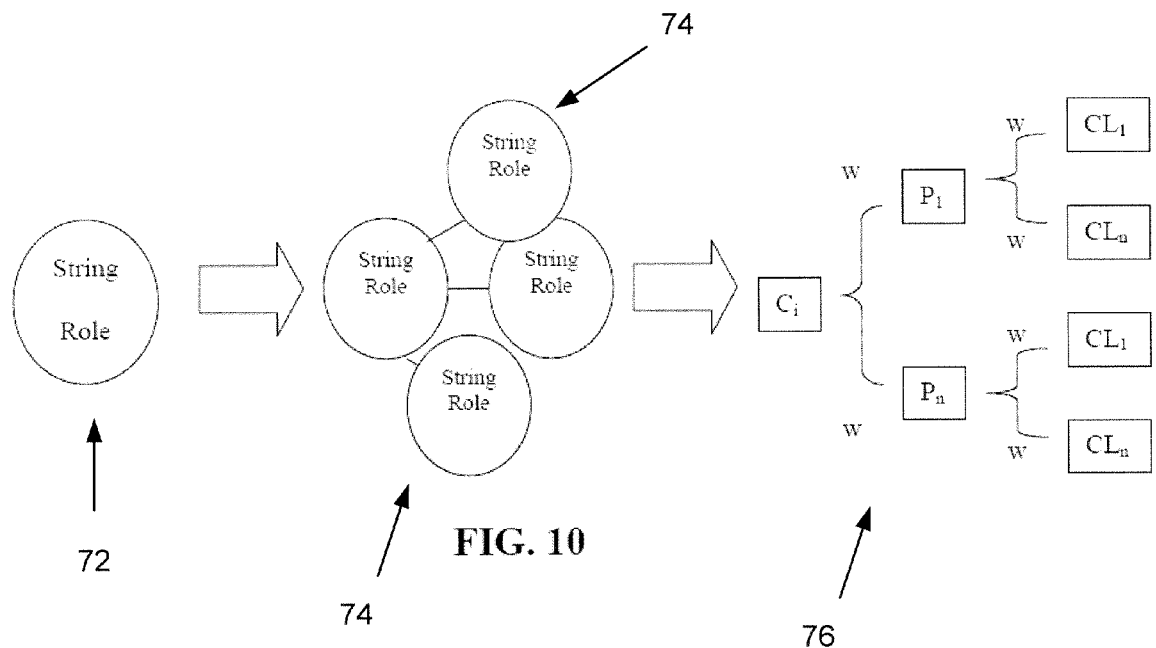
FIG. 10 is a flow diagram illustrating one aspect of Compression of Knowledge Representation in the second generation Dynamic Conceptual Network in accordance with an embodiment of the present invention.

An initial solution can be setting a "cap" on the storage allocated to document references and positions that "fade out" older document links and all of their connected elements. This can make the system entirely reinforcement driven. In some ways, this is acceptable, as critical pieces of knowledge are likely accessed regularly and therefore not forgotten. It is also the case that general knowledge obtained over the long term can be captured through some other storage structure. In the analyst area, some concepts and associations (even entire patterns of concepts) may be isolated and given priority storage despite the timestamp. It does, however, still make sense to have some mechanism that can learn facts and knowledge, even if sufficient storage is not available (or, alternatively, if it does not make sense to allocate given performance degradation), to give the system the ability to recall the exact resource it obtained the knowledge from, or the specific context from which it was obtained. Addressing this involves creating a hyper-recursive schema that deals more in prototypes than in particular schema individuals. In other words, generalization and reflexivity are necessities for memory to be economical enough to use in cognitive activities. First, a deeper look at the data is required, to see what patterns emerge at the higher experience levels, i.e. full document and document cluster levels. To reconstruct a linguistic experience, the system needs to perform a series of steps termed "concept sequencing." FIG. 10 illustrates an example of the progression. Concept sequencing begins with the selection of a particular string with a specific role 72. That string/role pair has a set of URL/positions about it in memory, that can be used to find the other string/role pairs 74 that occur close enough to its own position, in order to reconstruct every semantic unit focused about the original string/role pair. As redundant nodes are isolated and combined, certain semantic units are weighted more heavily and the graph 76 created by this sequencing takes shape.

Figures 11, 12:
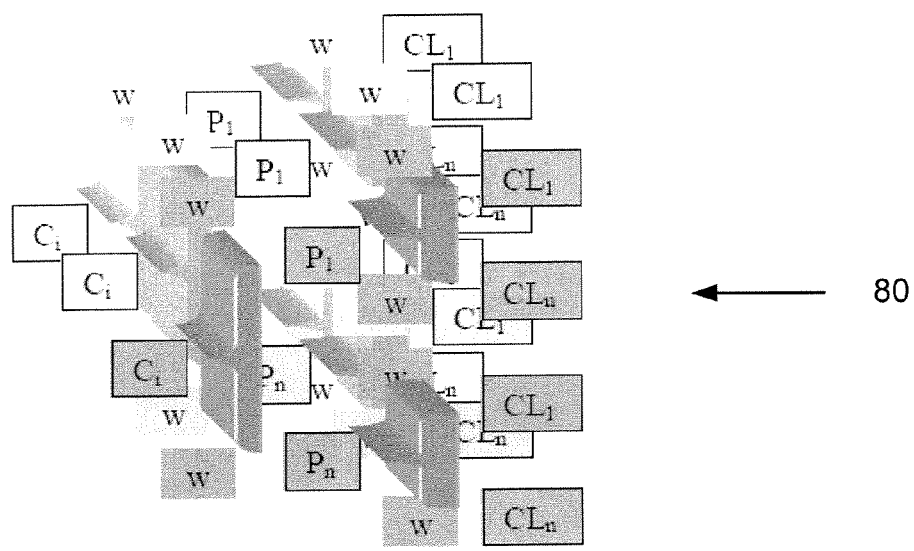
FIG. 11 is a diagram of a progression in the form of a multi-dimensional network representation built in 3×N×N segments in accordance with an embodiment of the present invention.
FIG. 12 is a table illustrating a long-term storage structure according to one aspect of the second generation Dynamic Conceptual Network in accordance with an embodiment of the present invention.

The example from above refers to the case when the role of the initial focus string is a concept. A similar weighted structure arises if the role were different for the initial focus string, but the labels change. This structure this gives is a kind of dynamic semantic inheritance network. When more strings are encountered in sequence, then the tree quickly becomes a multi-dimensional network 80 with parallel inference capacity, as illustrated in FIG. 11. As shown, the multi-dimensional network is built in 3×N×N segments linked as primitive assemblies that are dynamically instantiated by experience interacting with the memory of the agent. The Agent Inference Module (AIM) determines the weighting between elements and the number of segments.

Nothing prevents the system from being able to move to higher abstraction levels where $C_I$ goes from a single string/role pair to an array of string/role pairs such as is found in an entire semantic unit. It is actually at this level, that it is appropriate to focus our long-term memory compression efforts. It is also important to note that there are cross-plane weights that are not easily seen in the above diagram. This is important because the true "network" of conceptual relationships begins to emerge. And, just like in other network designs, the focus concept (s) can be seen as the input layer and the branches off from the focus concepts as "hidden layers" that are dynamically constructed from the concept space. The output layer would be the response from the system and is dealt with in the Agent Inference Module (AIM) detailed in the next section. The AIM also is what dynamically calculates the weights along the nodes based on the context.

Given this memory structure, it is clear that one can conserve storage and retain learning merely by storing the first order node links from complete semantic strings to other semantic strings. What this means is that long-term memory is primarily associative with hierarchy created by strength of association across multiple nodes. The search algorithm involved must therefore search in semantic units and look for other semantic units that match up. The long-term storage structure 84 is shown by FIG. 12. Within the semantic unit, however, is the structure of the semantic units constituents (strings and roles of a given semantic unit are encoded in the array) and therefore the knowledge acquired for every concept historically. The time value is only for the initial entry of the link, not every instance. Retrieving this knowledge for a given concept can be computationally heavy for a broad concept (like "man") and smaller for more narrowly defined concepts (like "The Washington Monument"). As the knowledge of the machine increases, however, greater and greater levels of processing power are necessary to exhaustively retrieve knowledge on a given concept.

Having outlined the principle algorithms for the storage of beliefs acquired by the DCN2, a few more points are necessary. First, within each a set of SM arrays, many may have minor differences (e.g. the use of analogous modifiers which are stored separately because different strings denote them). Some cheating may be done here through the use of a thesaurus module, to replace many words with one representative word, and variation can be accomplished through semi-random selection of semantically identical terms. This can result in a large compression of the long-term storage structure by limiting the range of possible string/role combinations to a smaller effective vocabulary. The resulting amalgamation of similar SM arrays can create a more differentiated network with sparser clusters. The SM arrays can become a set of semantic prototypes where interpolation may be done fairly readily. Any loss in granularity at the long-term level is fairly unnoticeable to the end user, since the mid-term "photographic" memory supplies sufficient granularity to the immediate contexts and recent history of contexts. An alternate method to counter any loss in granularity can have the system archive different mid-term memories on specific high-level categories. This would require roughly the same level of storage as one very large mid-term memory, but the search space would locally be much less, thereby not impacting performance for the user. This is a similar approach to having multiple knowledge bases with only one loaded into memory, at a time based upon need. A difference here is that this knowledge base is dynamically generated and every element is organically connected. There are many other such techniques that may be utilized, as well. As a second point, realizing the Conceptual Continuum (CC) necessary for the DCN2 requires that the many levels of linguistic activity be placed along emergent "natural property" dimensions. These natural property dimensions can be thought of as ultimately independent vectors within a vector space. There are useful tools for discovering the independent vectors that make up the dimensionality of the concept vector space and the ultimate rank of a massive matrix that can represent them, including Self Organizing Maps (SOMs), eigenvector and eigenvalue analysis algorithms, and Distributed Clustering Algorithms. Some of these ideas are implemented in the AIM.

Dynamic Contextual Inference

Figure 13:
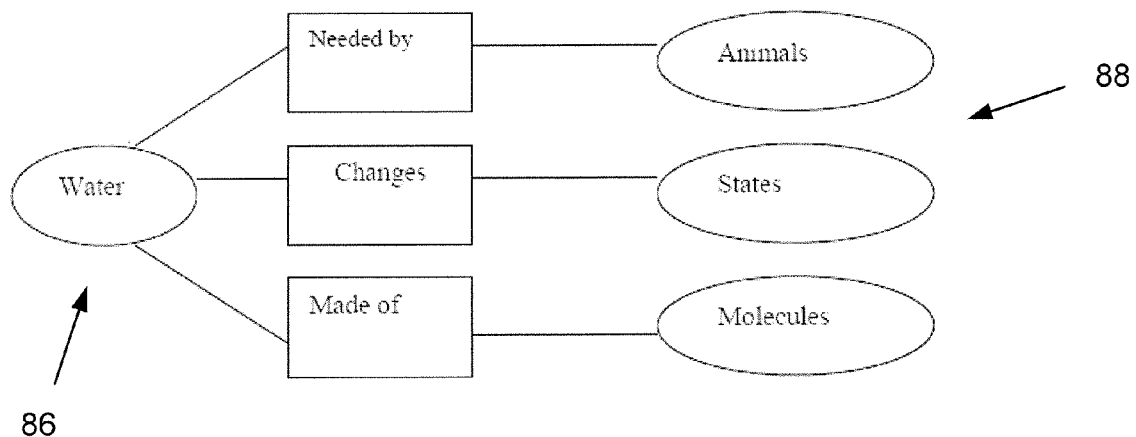
FIG. 13 is a diagram of a semantic network illustrating one aspect of Dynamic Contextual Inference in the second generation Dynamic Conceptual Network in accordance with an embodiment of the present invention.

Inference in the DCN2 is essentially the methodology the agent system uses to construct its memory substrate to apply to specific contexts and weight the segments that make up that substrate dynamically based on context. This presupposes a mechanism for determining context that is causally tied to the creation of the inference engine. The inference engine operates somewhat like a semantic inheritance network that is continually expanded and collapsed based on the perceptions. A key difference, however, is that nodes in the network are dynamically selected subspaces of a global concept space. To visualize this, one may consider a typical semantic network 88 that has a single concept 86 as a starting point, as illustrated in FIG. 13.

Figure 14:
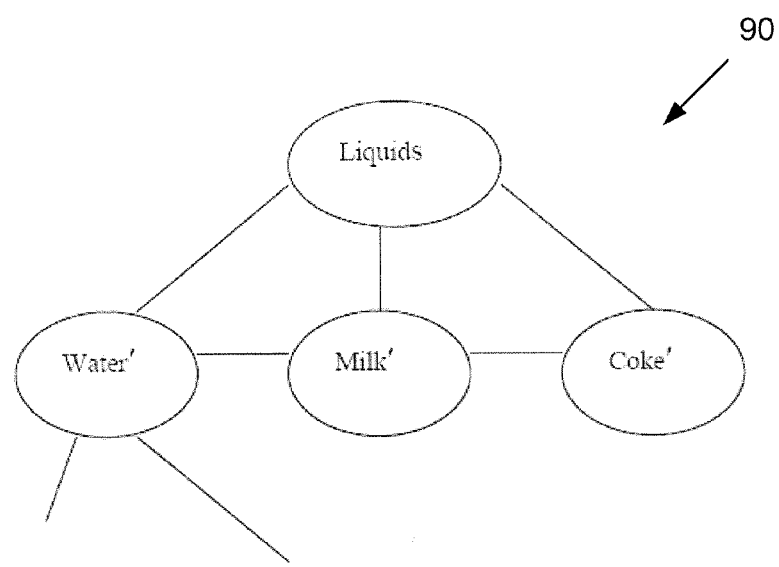
FIG. 14 is a diagram of a compressed semantic network illustrating another aspect of Contextual Inference in the second generation Dynamic Conceptual Network in accordance with an embodiment of the present invention.

This network can be compressed into a semantic network with embedded frames for a broader ontology-like representation. In the representation of FIG. 14, the compressed water network 90 is denoted as water', and the convention is held by applying (') to other concepts.

Figure 15:
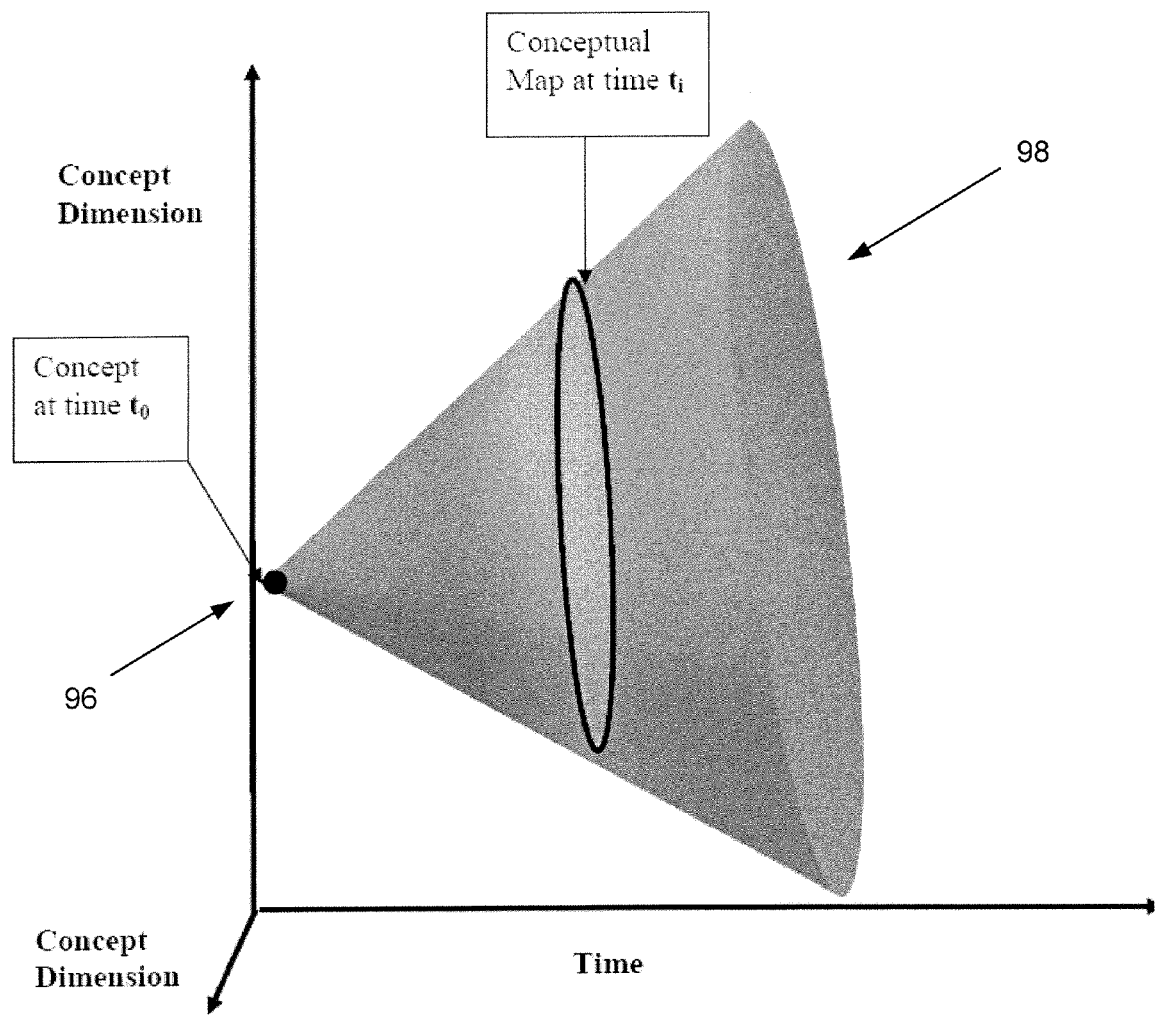
FIG. 15 is a graph illustrating a dynamic ontology with flexible bindings in accordance with an embodiment of the present invention.

The creation of ontologies is normally a function of knowledge engineering performed by humans. What the AIM does is create ontologies dynamically. The elements of the ontology are concepts, but concepts are actually a discovered pattern of relationships between semantic units and their elements. Whereas the visualization of the semantic network and conventional ontologies is a tree, the best visualization of a dynamic ontology with flexible bindings is a series of connected cones. Each individual cone 98 is actually a subspace of a global concept space extended from a single concept 96, as illustrated by FIG. 15.

In this visualization, it is clear that there is a rapidly accelerating surface area of the concept map (the strong associative node structure at any given instant) that at some point might make traversing the map intractable. This is why convention SOM solutions (as well as other Hopfield and BAM model ANNs) for acquiring the deep level of understanding DCN2 generally accomplishes do not scale well enough to be practically used. Thus, the selection and expansion of semantic progression vectors must be constrained. Since this representation is actually a compressed visualization (in actuality the "surface" is an n-dimensional hyperspace with 'n' being the number of natural property dimensions), discovering the natural property dimensions and modeling their dynamics is the first step towards addressing this. Once the minimal basis vectors for the conceptual space, the pathways through which they are executed can be recorded, and they can be clustered, to create another dimensional filter. In many ways, this is like creating thin hidden layers (i.e. hidden layers with substantially reduced numbers of neurons) dynamically to route activations more rigidly. This process can be repeated until such time that the creation of new filters causes negligible gain in limiting the range of semantic progression outside of the minimal set. The clusters within the filter—which emerge from the entirety of the experience of the DCN2— create a hierarchy that is analogous to an ontology, without any sacrifice of global organization across the concept space. In fact, conventional ontologies may be used as patterns to which the hierarchy of filters can be aligned. This adds a supervised learning element to the system, which renders the DCN2 human-trainable, showing that its emergent meanings are parallel to actual human beliefs.

In addition to the creation of these emergent structures—which provide powerful categorization functions—there is a substantial need to align the selection of a particular space based on a particular input array. There is an approximate inverse relationship between the scaling potential of the space over time (which is the uncertainty) and the initial determination of the input array (its size and completeness). If the initial input is an entire document describing the search, it is highly likely that the search will yield an extremely accurate return array. If the search is minimally determined, i.e. the input array is only a single concept or semantic unit, then it is likely that the system will require additional information that may be acquired through dialogue with the user. Looking at the cone image of FIG. 15, the relationship between the initial input set and the uncertainty is that the cone is made narrower by more highly determined input arrays and wider by more minimally determined ones.

Each potential semantic progression is modeled as an event space that is a subspace of the global normalized concept space. As the DCN2 experiences additional documents, it begins to develop patterns of these progressions that are recorded and clustered to reduce the variance in distance in state space for the entire progression. This can be accomplished by discovering a recursive function that represents the maximum number of experienced states with the minimal ad hoc basis vector shifts i.e. prototype discovery. From a mathematical perspective, the eigenvalues ($\lambda$) of the state vector at time $t_i$ versus the state vector at time $t_0$ represent the appropriate linear operator, and the prototype is a clustering about certain eigenvalues.

The output of the AIM is simply dependent on the specific requests of the method invoked. The general algorithm is to take in a query request and then use that request as the initial belief state vector, and to retrieve associated beliefs and/or sources from the agent system's memory. In more complex applications, the process is simply to construct the minimal path in terms of available methods and belief states from the initial input state vector through to the desired end state vector. The dimensions and values of these methods are determined when they are coded as application and feature extensions. The AIM is therefore a module that is able to create optimal vector spaces to represent feature spaces and develop natural pathways for progressions between these spaces. This is a general framework that applies not just to the linguistic space, but also to all renderings of pattern discovery into a meaningful state space.

Agent Infrastructure—Knowledge Discovery Agent System (KDAS) Core

Figure 16:
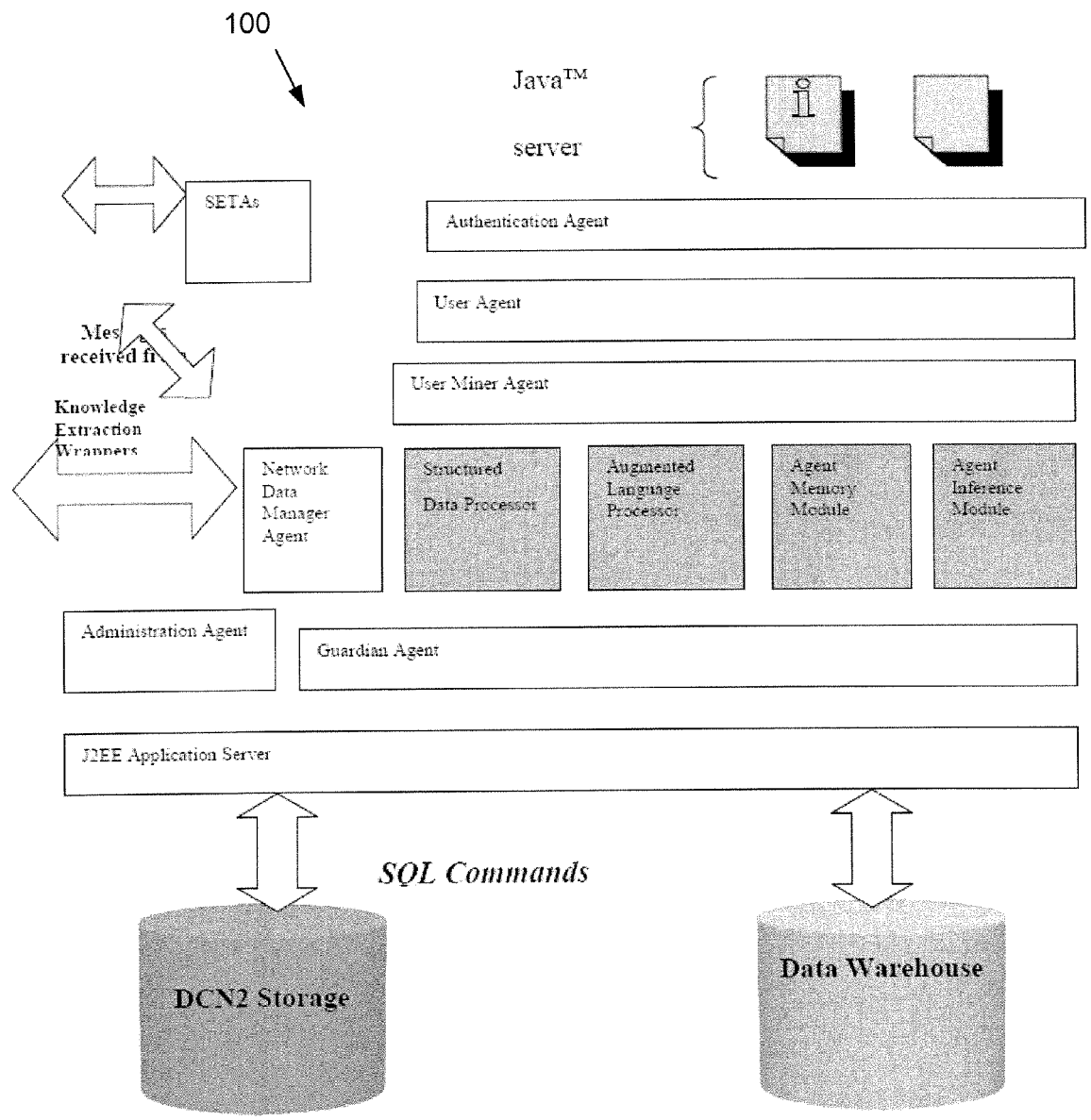
FIG. 16 is a diagram illustrating the core architecture of one aspect of the Knowledge Discovery Agent System in accordance with an embodiment of the present invention.

The KDAS core is built upon the architecture for the Personal Search Agent (PSA), which is augmented with the modified modules necessary for learning. This core, like the PSA system, is deployed on a certified J2EE application server and composed of Java Beans and Enterprise Java Beans (EJBs). The application is multithreaded with instances being distinguished by separate container spaces. As with other J2EE applications, the KDAS core may run on one server or on multiple servers within the same container space. The KDAS core connects to outside sources through additional Search Engine Task Agents (SETAs), Network Data Agents (NETAs), as well as Knowledge Extraction Wrappers (KEWs) that parse proprietary data formats into forms readable to the KDAS core. The architectural diagram 100 of the core is illustrated by FIG. 16.

Within a given configuration, individual agents can execute on dedicated servers optimized for their particular agents. Of these agents, the AIM is the most processor and memory intensive, while the AMM is memory and storage intensive. The scalability of the system may be somewhat limited by the AMM size because the AIM builds from the AMM. The other modules, however, do not substantially bottleneck aspects of the system's performance.

At the abstract level, the complexity of an agent can be measured by the dimensionality and granularity of its agent state space. This agent state space is held by the AMM. The AIM, in turn, builds optimal pathways through that state space and requires sufficient processing and memory resources to model those paths and execute them. While the KDAS core does not expressly require collectivization of learning and pathway construction, it is highly beneficial to connect all KDAS systems to a central hub, in order to create a global AMM and global pathway cache. Individual organizations may then utilize a subspace of the global agent learned agent space for general use, but utilize the collective experience to optimize the creation of prototypes and attractors within the agent space.

The Transition Path to First Generation Digital Reasoning Agents

At this juncture, it has been demonstrated that one or more embodiments of the present invention comprise a system that can appropriately dynamically model knowledge within the context of knowledge discovery in unstructured data sources. In addition, an agent infrastructure built on stable and secure technologies and able to be applied in Enterprise computing environments has been described. The core algorithms can be transposed into the domain of structured sources by only modifying the ALP module with a structured data extraction module that can appropriately parse the structured data into input arrays that can be organized by the AMM and AIM. The semantic unit names are changed, as well as the binding structures to reflect those that are explicit in the database, and this may be done through a combination of metadata extraction, end-user definition, and data modeling algorithms.

Another alternative approach involves integrating another piece of technology into the system, to dynamically model the data and then render that data model as concept extensions within the DCN2. A structured knowledge extraction system comparable with our unstructured extraction system can be constructed, and when both the structured and unstructured sources are intelligently integrated into the DCN2, the learning core is made complete. Moving from this core to Digital Reasoning Agents requires connecting the DCN2-like data dynamics to the other primitives in the DML form. Recalling the earlier decompositions, within the DML formal model all desires capable of being satisfied are decomposable to sequence(s) of intentions, which in turn are decomposable into a sequence of methods with associated beliefs. From a mathematical vantage point, methods are linear operators on state vectors. Since the DCN2 creates a state space from its experiences and the AIM creates filters through which transforms in state space tend to occur, it may now be seen that methods are merely hyper-rigid filters, meaning that they are completely static transform operations. This is differentiated from mere rigidity, in that the latter refers to the stability of certain attractors or prototypes that emerge and are utilized in filters by the AIM. They are predetermined through programming to accomplish necessary transforms in finite state machines—which is what an agent is, only an agent is not deterministic in as simple a way, but is much more like a chaotic system.

Thus, extending DCN2 into the methods component of the DML requires a mapping of system methods to before and after values of belief states within the DCN2, i.e. transform methods into pathways. This is not as easy as it may seem, because the proper level of abstraction must be chosen. If the knowledge abstraction granularity of the method belief level were made the same as the linguistic level, then one would in effect be looking for meaning in clusters of object code. Instead, the certain machine-readable descriptions should be written for any methods or modules of the agent system. The machine may then acquire associations between user requests (invoking elements of the module description including the desired output) and desired output states. Since intentions are sets of methods and associated beliefs, this same approach can be utilized for the application of DCN2 dynamics to the level of intentions. A DML object may therefore take shape as a dynamic data structure consisting of arrays of beliefs obtained from the user, the environment, and memory of the agent system that correspond to vectors in the agent state space. The Agent-Core (which includes DCN2) then utilizes the DML object to retrieve the necessary memory subspaces for the desire requested and chart a path through agent state space to satisfy that desire.

Further Discussion of KDAS

The Knowledge Discovery Agent System (KDAS) is a second generation integrated knowledge server system utilizing the Digital Reasoning™ technology, according to yet another aspect of the present invention. It links structured and unstructured knowledge discovery in a unified, learning cognitive model. As an agent system, it is highly extensible to new data sources and pattern discovery techniques and from a Human Computer Interaction (HCI) standpoint, KDAS provides a Universal Query Interface that allows users to easily acquire information from any source that the software is connected to, with intelligent filtering to ensure the relevance of what is returned. The system is minimally invasive to existing data sources and allows a variety of methods for the organization to manage how the KDAS server is given data. This ensures that the KDAS system can adapt and enforce security policies already in place at an organization.

Functionality

The KDAS system has a wide range of functionality for both the end user and the organization as a whole:

Full Semantic Analysis of Unstructured Sources

Utilizing the DCN2, the KDAS system can extract knowledge from unstructured sources and organize this knowledge preserving contextual dependencies. This knowledge is then applied to improve the intelligence of the system and increase the accuracy of future searches. The knowledge is also organized and retained in the memory of the agent system and can be recalled for an analyst on request.

Pattern Discovery from Structured Sources

The KDAS system can do pattern discovery on structured sources. The success of the pattern discovery for the end user depends on the provided semantics and metadata of the structured source. Implicit relationships within the data are discovered, but these implicit relationships often depend on the explicit relationships of the database for interpretation. When sufficient information is provided about the database structure, then the patterns that are discovered can be related and organized in the context of the explicit structure. In addition, the knowledge discovered is related back to knowledge from unstructured sources and linked so that a unified picture of knowledge is obtained.

Extensible API for Additional Source Types

The KDAS system features an API provided with the servers, that allows the organization utilizing it to add their own addition data source types. This gives the organization the freedom to isolate the KDAS system and feed it through gateways of its choosing; this, in turn, provides customers with additional options for controlling the security of their network.

Automatic Ontology Generation for Entire Organization

KDAS with its DCN2 core allows the organization or authorized users to visualize the ontology created by the experience of the DCN2. A user can select varied levels of granularity.

Universal Query Interface

Users interact with the KDAS system through a simple query interface that allows them to search the entire DCN2 or selected subsections, depending on their security authorization. The KDAS system accepts the query, parses it into a semantic unit that it can identify, and then checks whether there is sufficient determination within the query string to sufficiently localize the search. If there is insufficient determination, then the KDAS system responds with a request for clarification that augments the determination of the search, until it is sufficiently localized to search effectively. Additional features of the Universal Query Interface are discussed under the next three sections.

Agent Search Delegation and Knowledge Summarization

The KDAS system is not only able to conduct real time searches of the DCN2, but users can delegate searches to the agent system to perform more exhaustive searches of sources that are not be possible in real time. The agent can then decompose the results of the search into a dynamic ontology and knowledge summary of the query with prioritization of selected components based on the personal settings of the user.

Individual User Personalization

Given that each user tends to have tendencies in terms of the conceptual subspaces that they utilize, the KDAS system caches the preferences of each user into a user profile, which is used to adjust the weightings generated by the AIM with the DCN2 when it is inferring likely semantic progressions relative to the resealing of certain conceptual dimensions, relative to that user's particular associations.

User Directed Training

In addition to the passive personalization that the KDAS provides through observing the searching behavior of the user, the KDAS system supports user-defined pattern discovery. The end user is able to create a conceptual graph of a pattern or relationship and label the entire graph and its components. The KDAS system can then create an "artificial" pathway in concept space for that graph and trigger an alert whenever that particular pathway is activated.

Multi-Level Security System

KDAS is deploy-able in ultra-secure environments and therefore has built-in support for multi-level security. It is able to protect information at the user, source, data, concept, aggregate source, and aggregate concept level with policies set up by the organization.

TeamReasoning and Collaboration Tools

Few workers in large organizations do their work in isolation; most work collaboratively with their peers to solve problems. KDAS can leverage collective learning and efforts of multiple users working on the same project. Teams working on the same problem can be grouped so that the passive and user directed training are utilized for every member of the team. This group intelligence is termed TeamReasoning™. KDAS is also able to facilitate collaboration for members of the team by allowing them to store and share their knowledge summaries over the network.

In summation, the KDAS extends the functionality of PSA in fundamental ways, making it the ideal tool for creating a learning organization.

Architecture

The architecture of KDAS is made up of elements of PSA, plus several additional modules. This section deals with extensions to previous PSA agents and other modules.

User Agent (UA):

The UA in KDAS is augmented to provide the user with additional features in the presentation. The UA further possesses enhanced ability to capture user input, to allow the creation of conceptual graphs from user directed training that are transferred to the User Miner for processing. The user agent is composed of a combination of EJBs and Java™ Servlets.

Network Data Manager Agent (NDMA):

The Search Manager in KDAS is augmented to manage new sources coming into the system and is termed the Network Data Manager Agent. The NDMA is a manager for the search agents and can accept remote data streams and messages of pre-defined types. It has some cognitive capacities, including the ability to learn the most appropriate data source for queries on particular concept and cache information locally on very active links and concepts. The NDMA is a collection of EJBs and can handle numerous simultaneous threads, dependent on available system resources. The NDMA can also be scripted to spawn particular search agents or message remote agents at pre-defined time intervals to continually maintenance the data sources.

User Miner (UM):

The UM agent of KDAS is modified to align its analysis with the changes in the DCN2. Since its task is re-weighting the subspaces of the DCN2, it works closely with the AIM.

It also accepts the user directed training sets from the UA and stores them in the user profile after they are evaluated by the AIM. The user miner agent is composed of several EJBs and has direct access to the RDBMS.

Search Engine Task Agents (SETAs) and Network Data Agents (NETAs)

The number of SETAs in KDAS is expanded significantly and encompasses proprietary search sources. In addition, intranet and extranet sources are searched as allowed by the organization through NETAs.

Augmented Language Processor (ALP) Module

The ALP is the module that processes all unstructured information and transforms it into schema that can be analyzed by the DCN2. It also contains the heuristics to transform part-of-speech information into Subject-Predicate-Object form. The ALP has $3^{rd}$ Party dependencies on the Inxight LinguistX Platform SDK for document tokenization and part-of-speech tagging.

Structured Data Processor (SDP) Module

The SDP takes in structured data types and prepares it for analysis by the DCN2. Once the data has been transformed into acceptable array structures, the AMM and AIM can model the data dynamically and then unify the structured and unstructured resources indexed by common context.

Agent Memory Module (AMM)

The ALP, AMM, and AIM supercede the DM and the CATA of the PSA. The AMM takes the preprocessed schema from the ALP and SDP and stores it in a compressed notation. The AMM also alters the primitive count of schema pieces relative to one another, that is used by the AIM to construct the concept space.

Agent Inference Module (AIM)

The AIM contains within it the clustering and filtering algorithms that render the global concept space, create multi-level filters, and dynamically select the contextually relevant subspace for a particular query. The AIM creates the global concept space iteratively, i.e. over its history of experiences, and stores that structure which connects with the AMM long-term and mid-term memory as a hash table. The AIM also creates and maintains the hierarchy of filters from learning about semantic progression paths (i.e. pathways) and stores this as a linked network with the vector positions reconciled to the global concept space.

Guardian Agent (GA)

The GA is a light enforcement agent that runs as a background service behind every user session enforcing access and use policies. The guardian agent is a proactive security measure and is able to prohibit access based on pre-set policies that limit access based on user profile at the resource, single concept, or multi-concept level. It is composed of EJBs and has direct access to the RDBMS through SQL commands. The modules of the guardian agent comprise a monitoring and document interdiction engine, a logging function, and a policy-based inference structure.

Administration Agent (ADMIN)

The ADMIN is the security enforcement coordinator within KDAS. It is the agent that manages administrator access to the system, including the setting up of user accounts, user access privileges, security and privacy policies, and user access records. The ADMIN can be accessed by the system administrator of the organization and is used to set up security policies. Additional features of the ADMIN include setting up multiple levels of security clearances, aligning those clearance levels with particular sources, concepts, aggregated sources, and aggregated concepts, and connecting with existing authentication measures to control information access and use. The administration agent is composed of EJBs and has direct access to the RDBMS through SQL commands. Its modules are user data entry forms, policy generation engines, and multi-cast messaging of policies to the guardian agents for all open sessions.

Authentication Agent (AUT)

The AUT is a wrapper on a third-party authentication system that takes pre-authenticated users through the login password or other authentication methods and notifies the session agents of the identity of the user. It is composed of a very small set of EJBs sufficient to take the certificate from the third-party authentication software and look up the identity code from the user access control list. Once the user's identity is determined, the identity is passed to the necessary agents and the appropriate policies are pulled and enforced throughout the user session.

Differentiation

The KDAS System represents a unified knowledge access system combined with an advanced cognitive system for filtering. Unlike approaches that may rely on flat classification technologies or "black box" neural network technologies, KDAS represents a powerful hybrid approach that delivers on the best attributes of both. Moreover, KDAS represents a large step forward to software that can understand the meaning of human language and intelligently dialogue with the end users.

The following are some areas in which KDAS may be ground-breaking. The dynamic, learned concept space represents a powerful knowledge representation system that can take on the characteristics of numerous conventional approaches (such as semantic networks, case-based systems, and neural networks) within the same structure.

In addition, the Universal Query Interface unifies structured and unstructured using learning and intelligent filtering. Further, User Directed Training allows synthesis of supervised and unsupervised learning that lets the agent system acquire new expertise.

Moreover, Multi-level Security support is an intelligent search system that integrates security at both the individual and aggregate levels. Finally, TeamReasoning™ provides the system with a group-learning aspect that improves the accuracy and relevance of research for every member of a collection of users.

Commercial Applications of KDAS

What follows are brief descriptions of commercial applications based on the KDAS core of the present invention. Many require only simple extensions to the KDAS framework. The applications may be broken down into two groups: health care, and commercial.

Health Care Applications

Conversational Medical Information System (CMIS)

CMIS is essentially the KDAS system augmented with a chatbot system that is able to dialogue with the user in natural language. This requires extending the UA to connect to the chatbot engine and adding a Conversational Inference Module (CIM) to translate requests from the chatbot to the schema structure of the DCN2 and back. In addition, numerous data extractors are used to interface with proprietary medical systems, or the use of a 3 Party data extractor may be required.

Physerve Physician Information System

Physerve is a physician information system for health care provider networks, to connect their central systems with physician systems. It is an extension of the KDAS core with additional network data agents that can extract data from preselected systems within physician's offices.

Knowledge Discover for Life Sciences (KDLS)

KDLS is another system derivative of the KDAS core, which utilizes additional tools to do numerical and statistical analysis.

Commercial Systems—Enterprise Knowledge Agent Systems (EKAS)

EKAS is essentially a version of the KDAS, for the commercial market. It features enhanced natural language query capacity that can optionally include the chatbot used in CMIS.

Public Knowledge Agent Systems (PKAS)

The PKAS replaces conventional website search engine technology with the intelligent technology of the KDAS system. It solves the issue within proposals to the World Wide Web Consortium (W3C) to create ontologies for the "semantic web." Through PKAS, the existing web may be turned into a semantic web without developing huge, cumbersome inference engines to deal with many varied ontologies.

PKAS can serve as avatars for content for the World Wide Web, such that web servers can, somewhat literally, talk to each other on a user's behalf. This requires modification to the messaging and interpretation systems, including translating dynamic knowledge created by the agent system into a common knowledge format such as KIF or an XML standard.

Personal Agent Services (PAS)

PAS is within the realm of intelligent software services. It is aimed squarely at the consumer market, and it leverages the intelligence of the KDAS system on the user's desktop. It wraps over a user's desktop and creates a dynamic ontology of user-related information that is completely seamless, i.e. relevant Internet knowledge, local documents, networked documents, email, etc. are all used to create a user-centric concept space. The intelligence about the user the system gains is completely transportable and is synchronized across all of the user's devices. The PAS becomes a kind of "personal intelligent operating system" that can serve as an intermediary for the user in acquiring content or tailoring services.

The following are additional aspects of the present invention, as well as current and planned implementations of the technology.

Automatic Knowledge Base Generation and Optimization

In terms of automatic generation of knowledge from structured and unstructured sources, additional work is still possible for improvement. Among some possible modifications and augmentations are rendering the knowledge base into First Order Logic (FOL) notation through the dynamic creation of Concept Graphs (CGs) that retain all contextual dependencies. This would allow the system to use backward chaining methods to test for truth consistency and begin to develop a better sense for the veracity of some of the statements emerging in its knowledge base. The particular contexts can be treated as frames and analyzed so as to reconcile divergent beliefs through testing or dialogue initiated with users. In the end, it is very important that the machine know if it is being lied to or not, without the user having to warn it about every instance. This problem may be adequately addressed through the use of proper logical calculus and a correspondence between the rigid calculus and the creation of structures of the concept space.

Ontology Assimilation

Another area of great practical use of the present invention is giving the agent system greater ability to assimilate human-defined ontologies. This may essentially be done in two stages, parsing and training. The parsing element would be adding additional agents to parse XML ontologies like DAPRA Agent Markup Language (DAML), other standard formats like the Knowledge Interchange Format (KIF), and proprietary formats like the elements of OpenCyc.

Dynamic Code Generation

Since the AIM creates pathways that represent transforms in agent belief states and it has been demonstrated that methods can be defined in terms of these transforms ("rigid filters"), it makes sense that these transforms can be used to dynamically generate executable methods at run time once the transforms have stabilized sufficiently. When descriptions of methods are created and aligned to changes in agent state space, method code may be modified by the agents to interpolate between existing pathways in agent state space. This would essentially mean that the agent system comes up with derivative methods that were intentionally changed by the agent to accomplish a previously unachievable goal. This level of self-modification requires great cognitive complexity.

Feature Assimilation

In the margin between ontology assimilation and dynamic code generation is a powerful derivative technology that may be termed Feature Assimilation. Feature Assimilation essentially uses a more complex model of the AIM to map input: output of programs whose input and output states and semantics can be modeled effectively to create pathways in an agent state space. These pathways, once they have stabilized after an enormous number of training sets, can then be converted into executable code which can "mimic" the state transition created by the other program. In addition, the state transition can be maximally optimized (there are information theoretic limits on the optimization when 100% emulation is required) through the creation of filters to create a program that matches or exceeds the performance of the assimilated application.

Quantum Inference Model

As alluded to in earlier sections, supra, it is believed that to better emulate human thinking, a massively parallel processing model is necessary, to handle a near infinite number of potential state transition functions in superposition. This may be termed the Quantum Inference Model.

Quantum inference occurs by the parallel examination of an indefinite set of eigenvectors with eigenvalue operators that collapse into a semantic progression vector that is the best determination of the system. Since any finite, discrete n-dimensional state space can be rendered as a finite, discrete m-dimensional state space where m<n so long as the dimensions of m have sufficient additions to the vector array, then inference could be substantially speed up the inference or increase its granularity by introducing this type of inference mechanism.

The following publications are hereby incorporated by reference in their entirety for all purposes, to the same extent as if each individual publication were specifically and individually indicated to be so incorporated by reference: Gelertner, David, "The Second Coming," available online at http://www.edge.org/3rd_culture/gelernter/gelernter_p1.html); Sowa, John F., *Conceptual Structures: Information Processing in Mind and Machine*, Addison-Wesley, Reading, Mass. (1984); Kohonen, Tuevo, *Self-Organizing Maps*, $3^{rd}$ Edition. New York: Springer, 2001 (Springer series in information sciences, 30); Hulth, Nils and Peter Grenholm, "A Distributed Clustering Algorithm", "Discovering Conceptual Dimensions in KDAS," and "Scaling Conceptual Dimensions and Neural Network Weighting Algorithms" In Lund University Cognitive Studies, 74 (1998); Lenat, Douglas B. & R. V. Guha, *Building Large Knowledge-Based Systems*, Addison-Wesley, Reading, Mass. (1990); Sowa, John F., *Knowledge Representation: Logical, Philosophical, and Computation Foundations*, Brooks/Cole, Pacific Grove, Calif. (2000).

The foregoing invention has been described in terms of the preferred embodiment. However, it will be apparent to those skilled in the art that various modifications and variations can be made to the disclosed method without departing from the scope or spirit of the invention. It is understood that the examples and embodiments described herein are for illustrative purposes only and that various modifications or changes in light thereof will be suggested to persons skilled in the art and are to be included within the spirit and purview of this application and scope of the appended claims.

The invention claimed is:

1. A system for processing information, comprising:
a computer for running software programs in a distributed network, said computer including a processing means in communication with said distributed network;
at least one storage means in communication with said processing means for storing programs and information; and
at least one data agent in said distributed network for conducting a specific response to commands generated by said processing means;
wherein said computer, said at least one storage means, and said at least one data agent are operable for:
learning associations of natural language artifacts in unstructured data sources, wherein said artifacts include at least one of words, phrases, subjects, predicates, modifiers, and other syntactic forms; and
learning semantic and syntactic relationships in structured data sources, wherein said structured data sources are in conventional formats used by relational database systems;
further wherein learned associations resulting from said learning associations of natural language artifacts are formed using grouping of one natural language artifact in a interaction window with another at least one natural language artifact in said interaction window, based on a criteria of shared features of one or more sets from said grouping constituting measurements from said data sources;
further wherein said criteria of shared features are dynamically determined without the use of a priori classifications and using conditional probability constraints between sets of learned associations; and
further wherein said grouping creates a network of conditional probabilities between all encountered natural language artifacts or a subset thereof, determined by consideration of conditional interaction probabilities based on a history of measurements from said data sources;
means for constructing hierarchies of association across a state space of term usage compatible for interpolation of mapping functions between sets of terms, wherein said mapping functions include one or more of fuzzy-type, weighted-type, or other types of mapping functions; and
means for generating a structure of mapping functions comprising sets of terms in particular semantic positions, wherein said structure comprises a formal semantic structure of one or more of programming languages, modal logics, frame systems, and ontologies of objects and relationships.

2. The system of claim 1, further comprising:
means for representing learned associations in a specific format;
wherein said specific format is compatible for operations for mapping between a plurality of data structures and languages comprising one or more of arrays, vector spaces, first order predicate logic, Conceptual Graphs, SQL, and typed programming languages; and
further wherein said typed program languages comprise one or more of Java, C++, and other conventional programming languages.

3. The system of claim 1, further comprising:
means for collecting data input generated by interaction with a human user; and
sensors for learning from said input.

4. The system of claim 1, further comprising:
a chatbot comprising a chatbot engine for engaging in dialogue with a user through natural language;
a conversational inference module for translating requests from said chatbot to said computer, said at least one storage means, and said at least one data agent; and
at least one data extractor connected to an existing third-party information system and operable for interfacing therewith in response to requests processed by said chatbot and said conversational inference module.

5. The system of claim 1, said at least one data agent further operable for interfacing with medical information systems selected from the group comprising physician offices systems, hospital systems, corporate systems, and health care provider network systems.

6. The system of claim 1, further comprising:
at least one network data agent, operable for connecting at least one preselected physician information system to at least one health care provider network, and further operable for extracting data from said at least one preselected physician information system and providing said data to said at least one health care provider network.

7. The system of claim 1, said at least one data agent further operable for clustering and visualizing data pertaining to defense intelligence.

8. The system of claim 3, further comprising:
means for utilizing results of said learning by said sensors to reorganize and alter mapping functions induced from analyzed input; and
means for aligning said mapping functions according to human natural usage information in said results of said learning;
wherein said data input is in the form of structured data or unstructured data.

9. The system of claim 4, wherein said existing third-party information system is a medical information system selected from the group comprising physician offices systems, hospital systems, corporate systems, and health care providers network systems.

10. The system of claim 7, further comprising:
a human analyst of defense intelligence data, wherein said clustering and visualizing are provided to said human analyst as supplemental means for analyzing said defense intelligence data.

11. A method, comprising the steps of:
providing a computer for running software programs in a distributed network, said computer including a processing means in communication with said distributed network;
providing at least one storage means in communication with said processing means for storing programs and information;
providing at least one data agent in said distributed network for conducting a specific response to commands generated by said processing means;
configuring said computer, said at least one storage means, and said at least one data agent to be operable for:
learning associations of natural language artifacts in unstructured data sources, wherein said artifacts include at least one of words, phrases, subjects, predicates, modifiers, and other syntactic forms; and
learning semantic and syntactic relationships in structured data sources, wherein said structured data sources comprise entities in conventional formats used by relational database systems;
wherein learned associations resulting from said learning associations of natural language artifacts are formed using grouping of one natural language artifact in a interaction window with another at least one natural language artifact in said interaction window, based on a criteria of shared features of one or more sets from said grouping constituting measurements from said data sources;
further wherein said criteria of shared features are dynamically determined without the use of a priori classifications, using conditional probability constraints between sets of learned associations; and
further wherein said grouping creates a network of conditional probabilities between all encountered natural language artifacts or a subset thereof, determined by consideration of conditional interaction probabilities based on a history of measurements from said data sources;
constructing hierarchies of association across a state space of term usage compatible for interpolation of mapping functions between sets of terms, wherein said mapping functions include one or more of fuzzy-type, weighted-type, or other types of mapping functions, and said sets of terms have corresponding particular syntactic positions; and
generating a structure of mapping functions composed of sets of terms in particular semantic positions, wherein said structure is a formal semantic structure of one or more of programming languages, modal logics, frame systems, and ontologies of objects and relationships.

12. The method of claim 11, further comprising the step of:
representing learned associations in a specific format;
wherein said specific format is compatible for operations for mapping between a plurality of data structures and languages comprising one or more of arrays, vector spaces, first order predicate logic, Conceptual Graphs, SQL, and typed programming languages; and
further wherein said typed program languages comprise one or more of Java, C++, and other conventional programming languages.

13. The method of claim 11, further comprising the steps of:
collecting data input generated by interaction with a human user; and
learning from said input.

14. The method of claim 11, further comprising the steps of:
providing a chatbot comprising a chatbot engine for engaging in dialogue with a user through natural language;
providing a conversational inference module for translating requests from said chatbot to said computer, said at least one storage means, and said at least one data agent;
providing at least one data extractor, for connecting to an existing third-party information system and for interfacing therewith in response to requests processed by said chatbot and said conversational inference module; and
connecting said at least one data extractor to said existing third-party information system.

15. The method of claim 11, further comprising the step of:
providing at least one network data agent, operable for connecting at least one preselected physician information system to at least one health care provider network, and further operable for extracting data from said at least one preselected physician information system and providing said data to said at least one health care provider network.

16. The method of claim 11, further comprising the step of:
clustering and visualizing data pertaining to defense intelligence.

17. The method of claim 13, further comprising the steps of:
utilizing results of said learning to reorganize and alter mapping functions induced from analyzed input; and
aligning said mapping functions according to human natural usage information in said results of said learning;
wherein said input data is in the form of structured information or unstructured information.

18. The method of claim 14, wherein said existing third-party information system is a medical information system selected from the group comprising physician offices systems, hospital systems, corporate systems, and health care providers network systems.

19. The method of claim 16, further comprising the step of:
- providing the results of said clustering and visualizing to a human analyst of defense intelligence data.

20. A dynamic conceptual network system, comprising:
- a computer for running software programs in a distributed network, said computer including a processing means in communication with said distributed network;
- at least one storage means in communication with said processing means for storing programs and information;
- at least one data agent in said distributed network for conducting a specific response to commands generated by said processing means; and
- means for generating a structure of mapping functions composed of sets of terms in particular semantic positions, wherein said structure is a formal semantic structure of one or more of programming languages, modal logics, frame systems, and ontologies of objects and relationships;
- wherein said computer, said at least one storage means, and said at least one data agent are further constructed and adapted for learning semantic and syntactic relationships in structured data sources, wherein said structured data sources are in conventional formats used by relational database systems;
- further wherein said computer, said at least one storage means, and said at least one data agent are constructed and adapted for learning associations of natural language artifacts in unstructured data sources, said natural language artifacts including at least one of words, phrases, subjects, predicates, modifiers, and other syntactic forms;
  - further wherein the learned associations resulting from said learning associations of natural language artifacts are formed using grouping of one natural language artifact in a interaction window with another at least one natural language artifact in said interaction window, based on a criteria of shared features of one or more sets from said grouping constituting measurements from said data sources;
  - further wherein said criteria of shared features are dynamically determined without the use of a priori classifications and using conditional probability constraints between sets of learned associations; and
  - further wherein said grouping creates a network of conditional probabilities between all encountered natural language artifacts or a subset thereof, determined by consideration of conditional interaction probabilities based on a history of measurements from said data sources.

21. The dynamic conceptual network system of claim 20, wherein the learned associations resulting from said learning associations of natural language artifacts are formed using grouping of one natural language artifact in a interaction window with another at least one natural language artifact in said interaction window, based on a criteria of shared features of one or more sets from said grouping constituting measurements from said data sources;
- further wherein said criteria of shared features are dynamically determined without the use of a priori classifications and using conditional probability constraints between sets of learned associations; and
- further wherein said grouping creates a network of conditional probabilities between all encountered natural language artifacts or a subset thereof, determined by consideration of conditional interaction probabilities based on a history of measurements from said data sources.

22. The dynamic conceptual network system of claim 20, further comprising means for representing learned associations in a specific format;
- wherein said specific format is compatible for operations for mapping between a plurality of data structures and languages comprising one or more of arrays, vector spaces, first order predicate logic, Conceptual Graphs, SQL, and typed programming languages; and
- further wherein said typed program languages comprise one or more of Java, C++, and other conventional programming languages.

23. The dynamic conceptual network system of claim 20, further comprising means for constructing hierarchies of association across a state space of term usage compatible for interpolation of mapping functions between sets of terms;
- wherein said mapping functions include one or more of fuzzy-type, weighted-type, or other types of mapping functions; and
- further wherein said sets of terms have corresponding particular syntactic positions.

24. The dynamic conceptual network system of claim 20, further comprising:
- means for collecting data input generated by interaction with a human user;
- sensors for learning from said input;
- means for utilizing results of said learning by said sensors to reorganize and alter mapping functions induced from analyzed input; and
- means for aligning said mapping functions according to human natural usage information in said results of said learning;
- wherein said data input is in the form of structured data or unstructured data.

25. The dynamic conceptual network system of claim 20, further comprising:
- a chatbot comprising a chatbot engine constructed and adapted for engaging in dialogue with a user through natural language;
- a conversational inference module constructed and adapted for translating requests from said chatbot to said computer, said at least one storage means, and said at least one data agent; and
- at least one data extractor connected to an existing third-party information system and constructed and adapted for interfacing therewith in response to requests processed by said chatbot and said conversational inference module.

26. The dynamic conceptual network system of claim 20, wherein said existing third-party information system is a medical information system selected from the group comprising physician offices systems, hospital systems, corporate systems, and health care providers network systems.

27. The dynamic conceptual network system of claim 20, further constructed and adapted for interfacing with medical information systems selected from the group comprising physician offices systems, hospital systems, corporate systems, and health care provider network systems.

28. The dynamic conceptual network system of claim 20, further comprising:
- at least one network data agent, constructed and adapted for connecting at least one preselected physician information system to at least one health care provider network, and further constructed and adapted for extracting data from said at least one preselected physician information system and providing said data to said at least one health care provider network.

29. The system of claim 20, further constructed and adapted to cluster and visualize data pertaining to defense intelligence and further comprising a human analyst of defense intelligence data, wherein said clustering and visualizing are provided to said human analyst as supplemental means for analyzing data.

30. A method for processing information, comprising the steps of:
providing a computer for running software programs in a distributed network, said computer including a processing means in communication with said distributed network;
providing at least one storage means in communication with said processing means for storing programs and information;
providing at least one data agent in said distributed network for conducting a specific response to commands generated by said processing means;
configuring said computer, said at least one storage means, and said at least one data agent to be operable for:
  learning associations of natural language artifacts in unstructured data sources, wherein said artifacts include at least one of words, phrases, subjects, predicates, modifiers, and other syntactic forms; and
  learning semantic and syntactic relationships in structured data sources, wherein said structured data sources comprise entities in conventional formats used by relational database systems;
    wherein learned associations resulting from said learning associations of natural language artifacts are formed using grouping of one natural language artifact in a interaction window with another at least one natural language artifact in said interaction window, based on a criteria of shared features of one or more sets from said grouping constituting measurements from said data sources;
    further wherein said criteria of shared features are dynamically determined without the use of a priori classifications, using conditional probability constraints between sets of learned associations; and
    further wherein said grouping creates a network of conditional probabilities between all encountered natural language artifacts or a subset thereof, determined by consideration of conditional interaction probabilities based on a history of measurements from said data sources;
  constructing hierarchies of association across a state space of term usage compatible for interpolation of mapping functions between sets of terms, wherein said mapping functions include one or more of fuzzy-type, weighted-type, or other types of mapping functions, wherein said sets of terms have corresponding particular syntactic positions; and
  generating a structure of mapping functions composed of sets of terms in particular semantic positions, wherein said structure is a formal semantic structure of one or more of programming languages, modal logics, frame systems, and ontologies of objects and relationships.

31. The method of claim 30, further comprising the step of:
representing learned associations in a specific format;
wherein said specific format is compatible for operations for mapping between a plurality of data structures and languages comprising one or more of arrays, vector spaces, first order predicate logic, Conceptual Graphs, SQL, and typed programming languages; and
further wherein said typed program languages comprise one or more of Java, C++, and other conventional programming languages.

32. The method of claim 30, further comprising the steps of:
providing a chatbot comprising a chatbot engine for engaging in dialogue with a user through natural language;
providing a conversational inference module for translating requests from said chatbot to said computer, said at least one storage means, and said at least one data agent;
providing at least one data extractor, for connecting to an existing third-party information system and for interfacing therewith in response to requests processed by said chatbot and said conversational inference module; and
connecting said at least one data extractor to said existing third-party information system;
wherein said existing third-party information system is a medical information system selected from the group comprising physician offices systems, hospital systems, corporate systems, and health care providers network systems.

33. The method of claim 30, further comprising the step of:
providing at least one network data agent for connecting at least one preselected physician information system to at least one health care provider network, and further operable for extracting data from said at least one preselected physician information system and providing said data to said at least one health care provider network.

34. The method of claim 30, further comprising the steps of:
clustering and visualizing data pertaining to defense intelligence; and
providing the results of said clustering and visualizing to a human analyst of defense intelligence data.

35. A method for processing information, comprising the steps of:
providing a computer for running software programs in a distributed network, said computer including a processing means in communication with said distributed network;
providing at least one storage means in communication with said processing means for storing programs and information;
providing at least one data agent in said distributed network for conducting a specific response to commands generated by said processing means;
configuring said computer, said at least one storage means, and said at least one data agent to be operable for:
  learning associations of natural language artifacts in unstructured data sources, wherein said artifacts include at least one of words, phrases, subjects, predicates, modifiers, and other syntactic forms; and
  learning semantic and syntactic relationships in structured data sources, wherein said structured data sources comprise entities in conventional formats used by relational database systems;
    wherein learned associations resulting from said learning associations of natural language artifacts are formed using grouping of one natural language artifact in a interaction window with another at least one natural language artifact in said interaction window, based on a criteria of shared features of one or more sets from said grouping constituting measurements from said data sources;

further wherein said criteria of shared features are dynamically determined without the use of a priori classifications, using conditional probability constraints between sets of learned associations; and further wherein said grouping creates a network of conditional probabilities between all encountered natural language artifacts or a subset thereof, determined by consideration of conditional interaction probabilities based on a history of measurements from said data sources;

collecting data input generated by interaction with a human user;

learning from said input;

utilizing results of said learning to reorganize and alter mapping functions induced from analyzed input; and aligning said mapping functions according to human natural usage information in said results of said learning;

wherein said input data is in the form of structured information or unstructured information.

36. The method of claim 35, further comprising the steps of:

providing a chatbot comprising a chatbot engine for engaging in dialogue with a user through natural language;

providing a conversational inference module for translating requests from said chatbot to said computer, said at least one storage means, and said at least one data agent;

providing at least one data extractor, for connecting to an existing third-party information system and for interfacing therewith in response to requests processed by said chatbot and said conversational inference module; and connecting said at least one data extractor to said existing third-party information system;

wherein said existing third-party information system is a medical information system selected from the group comprising physician offices systems, hospital systems, corporate systems, and health care providers network systems.

37. The method of claim 35, further comprising the step of:

providing at least one network data agent for connecting at least one preselected physician information system to at least one health care provider network, and further operable for extracting data from said at least one preselected physician information system and providing said data to said at least one health care provider network.

38. The method of claim 35, further comprising the steps of:

clustering and visualizing data pertaining to defense intelligence; and providing the results of said clustering and visualizing to a human analyst of defense intelligence data.

* * * * *